US008367393B2

(12) United States Patent (10) Patent No.: US 8,367,393 B2
Hahn-Hägerdal et al. (45) Date of Patent: Feb. 5, 2013

(54) SACCHAROMYCES STRAIN WITH ABILITY TO GROW ON PENTOSE SUGARS UNDER ANAEROBIC CULTIVATION CONDITIONS

(75) Inventors: Bärbel Hahn-Hägerdal, Lund (SE); Oskar Bengtsson, Oslo (NO); Maurizio Bettiga, Göteborg (SE); Rosa Garcia Sanchez, Malmö (SE); David Rundquist, Malmö (SE); Marie-Francoise Gorwa-Grauslund, Lund (SE)

(73) Assignee: C5 Ligno Technologies Lund AB, Lund (SE)

( * ) Notice: Subject to any disclaimer, the term of this patent is extended or adjusted under 35 U.S.C. 154(b) by 0 days.

(21) Appl. No.: 13/130,729

(22) PCT Filed: Nov. 20, 2009

(86) PCT No.: PCT/SE2009/000498
§ 371 (c)(1),
(2), (4) Date: May 23, 2011

(87) PCT Pub. No.: WO2010/059095
PCT Pub. Date: May 27, 2010

(65) Prior Publication Data
US 2011/0294180 A1 Dec. 1, 2011

(30) Foreign Application Priority Data
Nov. 24, 2008 (SE) ...................................... 0802467

(51) Int. Cl.
*C12N 1/20* (2006.01)
(52) U.S. Cl. .................................. 435/252.35
(58) Field of Classification Search ............... 435/252.3, 435/252.35
See application file for complete search history.

(56) References Cited

U.S. PATENT DOCUMENTS
2005/0009135 A1 1/2005 Bro et al.

OTHER PUBLICATIONS

Watanabe et al., Biosci. Biotechnol. Biochem., 2007, 71(5), 1365-1369.*
International Search Report for International Application No. PCT/SE2009/000498 mailed Jan. 13, 2010.
Ammerer, G. "Expression of Genes in Yeast 5 Using the Adci Promoter." *Methods in Enzymology 101*. pp. 192-201 (1983).
Andreasen et al. "Anaerobic nutrition of *Saccharomyces cerevisiae*. I. Ergosterol requirement for growth in a defined medium." *J Cell Physiol 41* pp. 23-36. (1953).
Bengtsson et al. "Xylose reductase from *Pichia stipitis* with altered coenzyme preference improves ethanolic xylose fermentation by recombinant *Saccharomyces cerevisiae*." *Biotechnol Biofuels 2* pp. 9. (2009).
Bengtsson et al. "Differential behaviour of two commonly used promoters in xylose utilizing recombinant *Saccharomyces cerevisiae*." pp. 1-16.

Berben et al. "The YDp plasmids: a uniform set of vectors bearing versatile gene disruption cassettes for *Saccharomyces cerevisiae*." *Yeast 7*(5) pp. 475-477. (1991).
Bettiga et al. "Arabinose and xylose fermentation by recombinant *Saccharomyces cerevisiae* expressing a fungal pentose utilization pathway." *Microbial Cell Factories* vol. 8. No. 40. 1-12.(2009).
Bro et al.. "Improvement of galactose uptake in *Saccharomyces cerevisiae* through overexpression of phosphoglucomutase: example of transcript analysis as a tool in inverse metabolic engineering." *Appl Environ Microbiol 71*(11) pp. 6465-6472. (2005).
Dagert et al. "Prolonged incubation in calcium chloride improves the competence of *Escherichia coli* cells." *Gene 6*(1) pp. 23-28. (1979).
Dower et al. "High efficiency transformation of *E. coli* by high voltage electroporation." *Nucleic Acids Res 16* pp. 6127-6145. (1988).
Eliasson et al. "Anaerobic xylose fermentation by recombinant *Saccharomyces cerevisiae* carrying *XYL1, XYL2*, and *XKS1* in mineral medium chemostat cultures." *Appl Environ Microbiol 66*(8) pp. 3381-3386. (2000).
Entian et al. "Yeast mutant and plasmid collections." Yeast gene analysis Edited by Brown JPA and Tuite MF San Diego. California. *Academic Press 26* pp. 431-449. (1998).
Gietz et al. "New yeast—*Escherichia coli* shuttle vectors constructed with in vitro mutagenized yeast genes lacking six-base pair restriction sites." *Gene 74* pp. 527-534. (1988).
Géldener et al. "A new efficient gene disruption cassette for repeated use in budding yeast." *Nucleic Acids Research 24*(13) pp. 2519-2524. (1996).
Hahn-Hëgerdal et al. "Role of cultivation media in the development of yeast strains for large scale industrial use." *Microb Cell Fact 4*: 31 pp. 1-16 (2005).
Hauf, et al. "Simultaneous genomic overexpression of seven glycolytic enzymes in the yeast *Saccharomyces cerevisiae*." *Enzyme Microb Technol 26*: 688-698. (2000).
Jeppsson et al. "Reduced oxidative pentose phosphate pathway flux in recombinant xylose-utilizing *Saccharomyces cerevisiae* strains improves the ethanol yield from xylose." *Appl Environ Microbiol 68*(4) pp. 1604-1609. (2002).
Jeppsson et al., "The expression of a *Pichia stipitis* xylose reductase mutant with higher K(M) for NADPH increases ethanol production from xylose in recombinant *Saccharomyces cerevisiae*." *Biotechnol Bioeng 93*, pp. 665-673. (2006).
Karhumaa et al. "Investigation of limiting metabolic steps in the utilization of xylose by recombinant *Saccharomyces cerevisiae* using metabolic engineering." *Yeast*. 22(5) pp. 359-368. (2005).
Karhumaa et al. "Co-utilization of L-arabinose and D-xylose by laboratory and industrial *Saccharomyces cerevisiae* strains." *Microb Cell Fact* vol. 5 No. 18. pp. 1-11. (2006).
Miyazaki et al. "Creating random mutagenesis libraries using megaprimer PCR of whole plasmid."*BioTechniques 33* pp. 1033-1034, 1036-1038. (2002).
Mumberg et al. "Yeast vectors for the controlled expression of heterologous proteins in different genetic backgrounds." *Gene 156*(1) pp. 119-122. (1995).
Munjral et al., "Studies on glucose-metabolizing enzymes in cytosolic and bacterioidal fractions of mungbean.(*Vigna radiate* L.) and lentil (*Lens culinaris* L) nodules." *Indian Journal of biochemistry & biophysics*. 44 pp. 186-189 (2007).
Rizzi et al. "Purification and 20 properties of the NAD+-xylitol-dehydrogenase from the yeast *Pichia stipitis*." *J Ferment Bioeng 67* pp. 20-24. (1989).

(Continued)

*Primary Examiner* — Maryam Monshipouri
(74) *Attorney, Agent, or Firm* — Merchant & Gould P.C.

(57) ABSTRACT

The invention relates to an improved *Saccharomyces* strain displaying improved viability and growth during anaerobic fermentation of pentose carbon sources such as xylose and producing fermentation products such as ethanol.

10 Claims, 12 Drawing Sheets

OTHER PUBLICATIONS

Rupp. "*LacZ* Assays in Yeast." Guide to Yeast Genetics and Molecular and Cell Biology Part B. *Academic Press*. pp. 112-129. (2002).

Smiley et al. "Demonstration of D-xylose reductase and Dxylitol dehydrogenase in *Pachysolen tannophilus*." *Biotech Lett 4* pp. 607-610. (2009).

Sonderegger et al., "Molecular Basis for Anaerobic Growth of *Saccharomyces cerevisiae* on Xylose, Investigated by Global Gene Expression and Metabolic Flux Analysis." *Appl. Environ. Microbiol 70*(4) pp. 2307-2317 (2004).

Träff et al. "Deletion of the *GRE3* aldose reductase gene and its influence on xylose metabolism in recombinant strains of *Saccharomyces cerevisiae* expressing the *xylA* and *XKS1* genes." *Appl Environ Microbiol* 67(12): 5668-74. (2001).

van Dijken et al., "An interlaboratory comparison of physiological and genetic properties of four *Saccharomyces cerevisiae* strains." *Enz Microb Technol 26*,pp. 706-714. (2000).

Verduyn et al. "Effect of benzoic acid on metabolic fluxes in yeasts—a continuous culture study on the regulation of respiration and alcoholic fermentation." *Yeast 8*: pp. 501-517. (1992).

Wahlbom et al. "Generation of the improved 25 recombinant xylose-utilizing *Saccharomyces cerevisiae* TMB 3400 by random mutagenesis and physiological comparison with *Pichia stipitis* CBS 6054." *FEMS Yeast Res 3*(3) pp. 319-326. (2003).

Watanabe et al. "Ethanol production from xylose recombinant *Saccharomyces cerevisiae* expressing protein-engineered NADH-preferring xylose reductase from *Picha stipites*." *Microbiology* vol. 153 pp. 3044-3054. (2007).

Gietz et al., "Large-scale high-efficiency yeast transformation using the LiAc/SS carrier DNA/PEG method," *Nature Protocols*, vol. 2, No. 1, 2007, pp. 38-41.

Runquist et al., "Increased expression of the oxidative pentose phosphate pathway and gluconeogenesis in anaerobically growing xylose-utilizing *Saccharomyces cerevisiae*," *Microbial Cell Factories 8*:49, 2009, pp. 1-12.

Gietz et al., "Studies on the Transformation of Intact Yeast Cells by the LiAc/SS-DNA/PEG Procedure." *Yeast*, vol. 11, 1995, p. 355-360.

Sanchez et al., "PGM2 Overexpression Improves Anaerobic Galactose Fermentation in *Saccharomyces cerevisiae*." *Microbial Cell Factories*, vol. 9, No. 40, 2010, 26 pgs.

Sanchez et al., "Cross-Reactions Between Engineered Xylose and Galactose Pathways in Recombinant *Saccharomyces cerevisiae*." *Biotechnology for Biofuels*, vol. 3, No. 19, 2010,9 pgs.

Bärbel Hahn-Hagerdahl et al., "Towards industrial pentose-fermenting yeast strains.", *Applied Microbiology and Biotechnology*, vol. 74, No. 5, 2007, p. 937-953.

Kaisa Karhumaa et al., "High activity of xylose reductase and xylitol dehydrogenase improves xylose fermentation by recombinant *Saccharomyces cerevisiae*.", *Applied Microbiology and Biotechnology*, vol. 73, No. 5, 2007, p. 1039-1046.

Extended European Search Report mailed Apr. 12, 2012.

\* cited by examiner

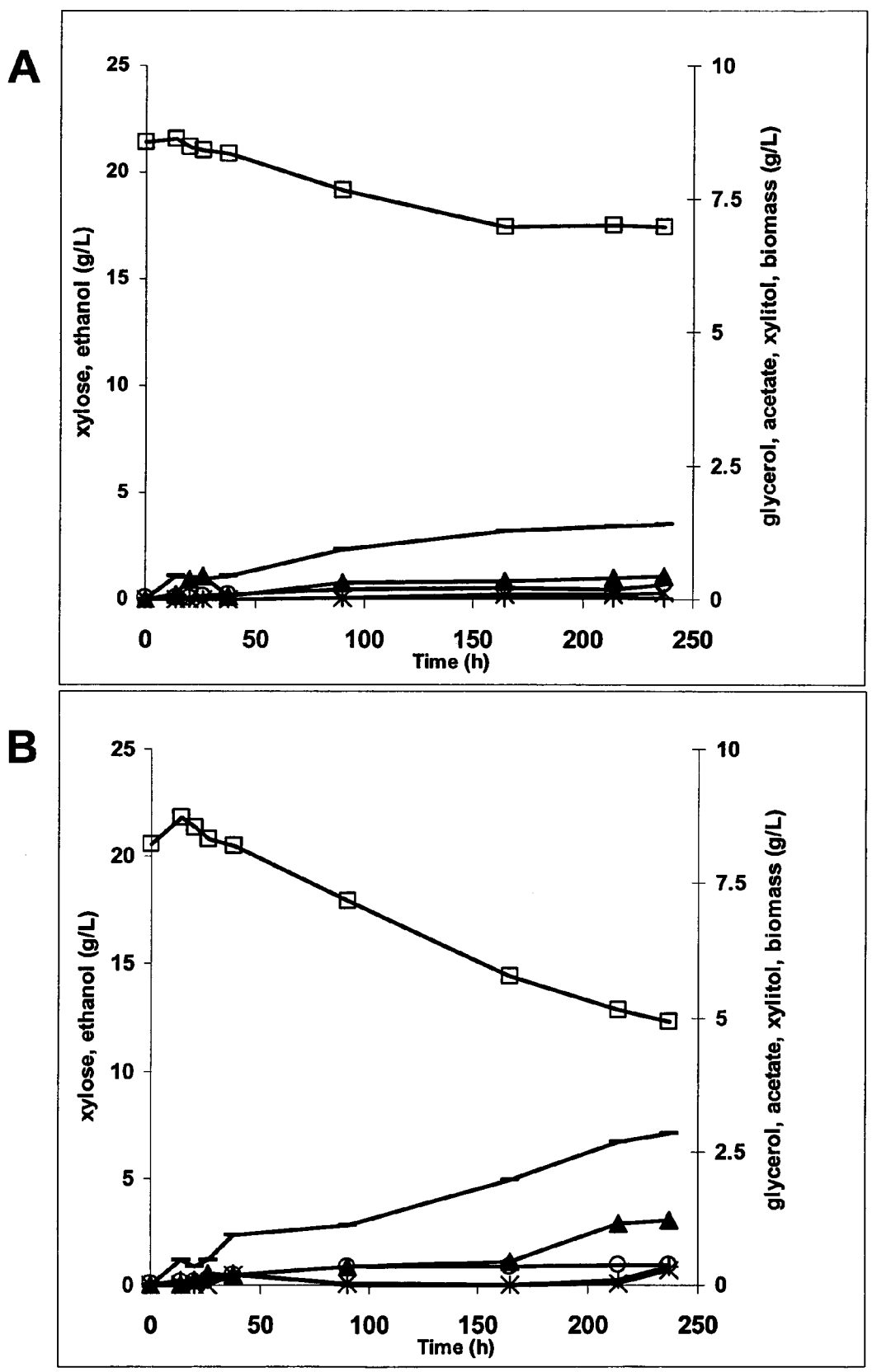
Fig 6A/6B

Fig 6B/6B
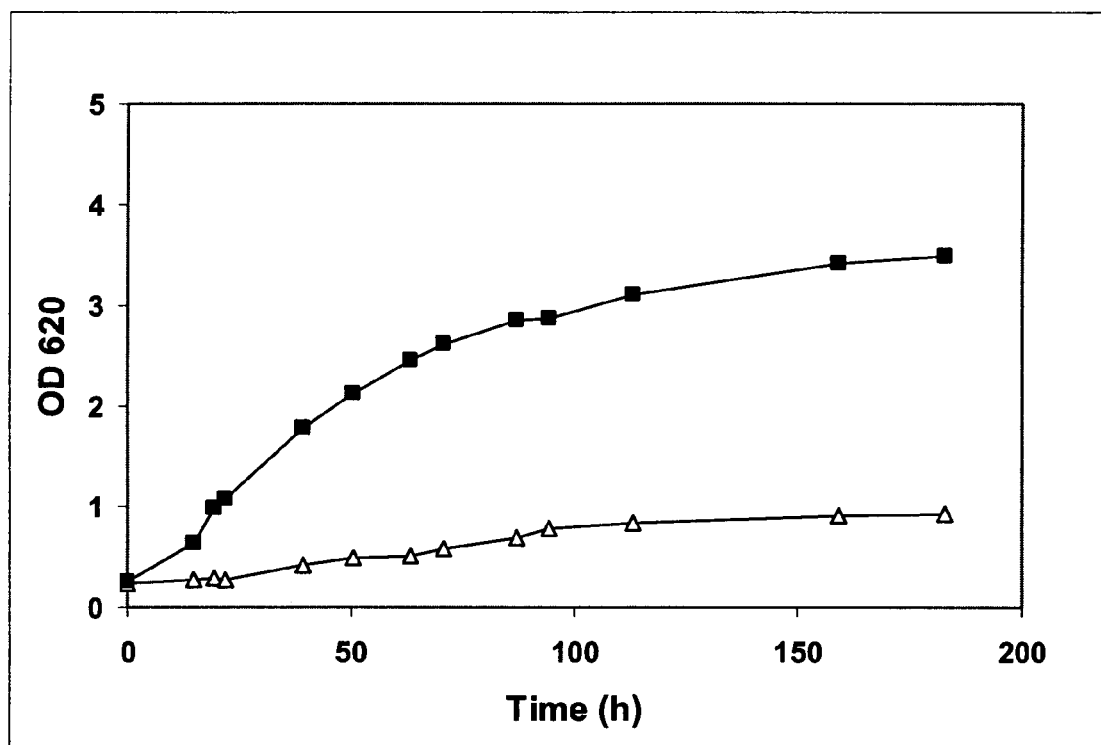

SEQUENCE LISTING

<160> NUMBER OF SEQ ID NOS: 34

<210> SEQ ID NO 1
<211> LENGTH: 2105
<212> TYPE: DNA
<213> ORGANISM: Artificial Sequence
<220> FEATURE:
<223> OTHER INFORMATION: TDH3 being derived from p42GPD (Mumberg et al., 1995) and XRK270R being derived from Pichia stipitis

<400> SEQUENCE: 1

```
aagcttggcg cgccagttta tcattatcaa tactcgccat ttcaaagaat acgtaaataa    60
ttaatagtag tgattttcct aactttattt agtcaaaaaa ttagccttt  aattctgctg   120 taaccegtac atgcccaaaa taggggggcgg gttacacaga atatataaca tcgtaggtgt   180
ctgggtgaac agtttattcc tggcatccac taaatataat ggagcccgct ttttaagctg   240
gcatccagaa aaaaaagaa tcccagcacc aaaatattgt tttcttcacc aaccatcagt   300
tcataggtcc attctcttag cgcaactaca gagaacaggg gcacaaacag gcaaaaaacg   360
ggcacaacct caatggagtg atgcaacctg cctggagtaa atgatgacac aaggcaattg   420
acccacgcat gtatctatct cattttctta caccttctat taccttctgc tctctctgat   480
ttggaaaaag ctgaaaaaaa aggttgaaac cagttccctg aaattattcc cctacttgac   540
taataagtat ataaagacgg taggtattga ttgtaattct gtaaatctat ttcttaaact   600
tcttaaattc tactttata  gttagtcttt tttttagttt taaaacacca gaacttagtt   660
tcgacggatt ctagaatgcc ttctattaag ttgaactctg gttacgacat gccagccgtc   720
ggtttcggct gttggaaagt cgacgtcgac acctgttctg aacagatcta ccgtgctatc   780
aagaccggtt acagattgtt cgacggtgcc gaagattacg ccaacgaaaa gttagttggt   840
gccggtgtca agaggccat  tgacgaaggt atcgtcaagc gtgaagactt gttccttacc   900
tccaagttgt ggaacaacta ccaccaccca gacaacgtcg aaaaggcctt gaacagaacc   960
ctttctgact tgcaagttga ctacgttgac ttgttcttga tccattccc  agtcaccttc  1020 aagttcgttc cattagaaga aaagtaccca ccaggatcct actgtggtaa gggtgacaac  1080
```

-continued

```
ttcgactacg aagatgttcc aattttagag acctggaagg ctcttgaaaa gttggtcaag    1140
gccggtaaga tcagatctat cggtgtttct aacttcccag gtgctttgct cttggacttg    1200
ttgagaggtg ctaccatcaa gccatctgtc ttgcaagttg aacaccaccc atacttgcaa    1260
caaccaagat tgatcgaatt cgctcaatcc cgtggtattg ctgtcaccgc ttactcttcg    1320
ttcggtcctc aatctttcgt tgaattgaac caaggtagag ctttgaacac ttctccattg    1380
ttcgagaacg aaactatcaa ggctatcgct gctaagcacg gtaagtctcc agctcaagtc    1440
ttgttgagat ggtcttccca agaggcattg ccatcattc caaggtccaa cactgtccca     1500
agattgttgg aaaacaagga cgtcaacagc ttcgacttgg acgaacaaga tttcgctgac    1560
attgccaagt tggacatcaa cttgagattc aacgacccat gggactggga caagattcct    1620
atcttcgtct aatctagagc tttggacttc ttcgccagag gtttggtcaa gtctccaatc    1680
aaggttgtcg gcttgtctac cttgccagaa atttacgaaa agatggaaaa gggtcaaatc    1740
gttggtagat acgttgttga cacttctaaa taagcgaatt tcttatgatt tatgattttt    1800
attattaaat aagttataaa aaaaataagt gtatacaaat tttaaagtga ctcttaggtt    1860
ttaaaacgaa aattcttatt cttgagtaac tctttcctgt aggtcaggtt gctttctcag    1920
gtatagcatg aggtcgctct tattgaccac acctctaccg gcatgccgag caaatgcctg    1980
caaatcgctc cccatttcac ccaattgtag atatgctaac tccagcaatg agttgatgaa    2040
tctcggtgtg tattttatgt cctcagagga caacacctgt tgtaatcgtt cttccacacc    2100
tgcag                                                               2105
```

<210> SEQ ID NO 2
<211> LENGTH: 2114
<212> TYPE: DNA
<213> ORGANISM: Artificial Sequence
<220> FEATURE:
<223> OTHER INFORMATION: HXTP being derived from p42GPD (Mumberg et al., 1995) and PGM2 being derived from pichia stipits

<400> SEQUENCE: 2

```
caggaacaat tcgggcccc tgcgtgttct tctgaggttc atcttttaca tttgcttctg     60
ctggataatt ttcagaggca acaaggaaaa attagatggc aaaaagtcgt cttcaagga     120 aaaatcccca ccatctttcg agatcccctg taacttattg gcaactgaaa gaatgaaaag    180
gaggaaaata caaatatac tagaactgaa aaaaaaaag tataaataga gacgatatat     240
gccaatactt cacaatgttc gaatctattc ttcatttgca gctattgtaa aataataaaa    300
catcaagaac aaacaagctc aacttgtctt ttctaagaac aaagaataaa cacaaaaaca    360
aaaagttttt ttaattttaa tcaaaaaagg atccccgggc tgcaatgtca tttcaaattg    420
aaacggttcc caccaaacca tatgaagacc aaaagcctgg tacctctggt ttgcgtaaga    480
agacaaaggt gtttaaagac gaacctaact acacagaaaa tttcattcaa tcgatcatgg    540
aagctattcc agagggttct aaaggtgcca ctcttgttgt cggtggtgat gggcgttact    600
acaatgatgt cattcttcat aagattgccg ctatcggtgc tgccaacggt attaaaaagt    660
tagttattgg tcagcatggt cttctgtcta cgccagccgc ttctcacatc atgagaacct    720
acgaggaaaa atgtactggt ggtattatct taaccgcctc acataatcca ggtggtccag    780
aaaatgacat gggtattaag tataacttat ccaatggggg tcctgctcct gaatccgtca    840
caaatgctat ttgggagatt tccaaaaagc ttaccagcta taagattatc aaagacttcc    900
cagaactaga cttgggtacg ataggcaaga acaagaaata cggtccatta ctcgttgaca    960
ttatcgatat tacaaaagat tatgtcaact tcttgaagga aatcttcgat ttcgacttaa    1020
```

```
tcaagaaatt catcgataat caacgttcta ctaagaattg gaagttactg tttgacagta    1080
tgaacggtgt aactggacca tacggtaagg ctattttcgt tgatgaattt ggtttaccgg    1140
cggatgaggt tttacaaaac tggcatcctt ctccggattt tggtggtatg catccagatc    1200
caaacttaac ttatgccagt tcgttagtga aaagagtaga tcgtgaaaag attgagtttg    1260
gtgctgcatc cgatggtgat ggtgatagaa atatgattta cggttacggc ccatctttcg    1320
tttctccagg tgactccgtc gcaattattg ccgaatatgc agctgaaatc ccatatttcg    1380
ccaagcaagg tatatatggt ctggcccgtt cattccctac ctcaggagcc atagaccgtg    1440
ttgccaaggc ccatggtcta aactgttatg aggtcccaac tggctggaaa tttttctgtg    1500
ctttgttcga cgctaaaaaa ttatctatct gtggtgaaga atcgtttggt actggttcca    1560
accacgtaag ggaaaaggac ggtgtttggg ccattatggc gtggttgaac atcttggcca    1620
tttacaacaa gcatcatccg gagaacgaag cttctattaa gacgatacag aatgaattct    1680
gggcaaagta cggccgtact ttcttcactc gttatgattt tgaaaaagtt gaaacagaaa    1740
aagctaacaa gattgtcgat caattgagag catatgttac caaatcgggt gttgttaatt    1800
ccgccttccc agccgatgag tctcttaagg tcaccgattg tggtgatttt tcatacacag    1860
atttggacgg ttctgtttct gaccatcaag gtttatatgt caagctttcc aatggtgcaa    1920
gattcgttct aagattgtca ggtacaggtt cttcaggtgc taccattaga ttgtacattg    1980
aaaaatactg cgatgataaa tcacaatacc aaaagacagc tgaagaatac ttgaagccaa    2040
ttattaactc ggtcatcaag ttcttgaact taaacaagt tttaggaact gaagaaccaa    2100
cggttcgtac ttaa                                                      2114

<210> SEQ ID NO 3
<211> LENGTH: 957
<212> TYPE: DNA
<213> ORGANISM: Artificial Sequence
<220> FEATURE:
<223> OTHER INFORMATION: Mutated Pichia stipitis XYL1

<400> SEQUENCE: 3
atgccttcta ttaagttgaa ctctggttac gacatgccag ccgtcggttt cggctgttgg      60
aaagtcgacg tcgacacctg ttctgaacag atctaccgtg ctatcaagac cggttacaga    120
ttgttcgacg gtgccgaaga ttacgccaac gaaaagttag ttggtgccgg tgtcaagaag    180
gccattgacg aaggtatcgt caagcgtgaa gacttgttcc ttacctccaa gttgtggaac    240
aactaccacc acccagacaa cgtcgaaaag gccttgaaca gaaccctttc tgacttgcaa    300
gttgactacg ttgacttgtt cttgatccac ttcccagtca ccttcaagtt cgttccatta    360
gaagaaaagt acccaccagg attctactgt ggtaagggtg acaacttcga ctacgaagat    420
gttccaattt tagagacctg gaaggctctt gaaaagttgg tcaaggccgg taagatcaga    480
tctatcggtg tttctaactt cccaggtgct ttgctcttgg acttgttgag aggtgctacc    540
atcaagccat ctgtcttgca gttgaacac cacccatact tgcaacaacc aagattgatc    600
gaattcgctc aatcccgtgg tattgctgtc accgcttact cttcgttcgg tcctcaatct    660
ttcgttgaat tgaaccaagg tagagctttg aacacttctc cattgttcga gaacgaaact    720
atcaaggcta tcgctgctaa gcacggtaag tctccagctc aagtcttgtt gagatggtct    780
tcccaaagag gcattgccat cattccaaag tccgacaccg tccaaagatt gttggaaaac    840
aaggacgtca acagcttcga cttggacgaa caagatttcg ctgacattgc caagttggac    900
atcaacttga gattcaacga cccatgggac tgggacaaga ttcctatctt cgtctaa      957
```

<210> SEQ ID NO 4
<211> LENGTH: 318
<212> TYPE: PRT
<213> ORGANISM: Artificial Sequence
<220> FEATURE:
<223> OTHER INFORMATION: Pichia stipitis XYL1 with mutations N272D and P275Q

<400> SEQUENCE: 4

```
Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asp
            260                 265                 270

Thr Val Gln Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```

<210> SEQ ID NO 5
<211> LENGTH: 318
<212> TYPE: PRT
<213> ORGANISM: Artificial Sequence
<220> FEATURE:
<223> OTHER INFORMATION: XRK270R being derived from Pichia stipitis

<400> SEQUENCE: 5

```
Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Pro Arg Ser Asn
            260                 265                 270

Thr Val Pro Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```

<210> SEQ ID NO 6
<211> LENGTH: 47
<212> TYPE: DNA
<213> ORGANISM: Artificial Sequence
<220> FEATURE:
<223> OTHER INFORMATION: Primer Sequence

<400> SEQUENCE: 6

```
gcataagctt ggcgcgccag tttatcatta tcaatactcg ccatttc          47
```

<210> SEQ ID NO 7
<211> LENGTH: 29
<212> TYPE: DNA
<213> ORGANISM: Artificial Sequence
<220> FEATURE:

```
<223> OTHER INFORMATION: Primer Sequence

<400> SEQUENCE: 7
gcattctaga atccgtcgaa actaagttc                                    29

<210> SEQ ID NO 8
<211> LENGTH: 29
<212> TYPE: DNA
<213> ORGANISM: Artificial Sequence
<220> FEATURE:
<223> OTHER INFORMATION: Primer Sequence

<400> SEQUENCE: 8
gcgcaagctt atgaccatga ttacggatt                                    29

<210> SEQ ID NO 9
<211> LENGTH: 29
<212> TYPE: DNA
<213> ORGANISM: Artificial Sequence
<220> FEATURE:
<223> OTHER INFORMATION: Primer Sequence

<400> SEQUENCE: 9
gtgagtcgac ttattttttga caccagacc                                   29

<210> SEQ ID NO 10
<211> LENGTH: 21
<212> TYPE: DNA
<213> ORGANISM: Artificial Sequence
<220> FEATURE:
<223> OTHER INFORMATION: Primer Sequence

<400> SEQUENCE: 10
gcggatcctc tagaatgcct t                                            21

<210> SEQ ID NO 11
<211> LENGTH: 24
<212> TYPE: DNA
<213> ORGANISM: Artificial Sequence
<220> FEATURE:
<223> OTHER INFORMATION: Primer Sequence

<400> SEQUENCE: 11
ttggatcctc tagattagac gaag                                         24

<210> SEQ ID NO 12
<211> LENGTH: 23
<212> TYPE: DNA
<213> ORGANISM: Artificial Sequence
<220> FEATURE:
<223> OTHER INFORMATION: Primer Sequence

<400> SEQUENCE: 12
catcattcca aggtccaaca ctg                                          23

<210> SEQ ID NO 13
<211> LENGTH: 23
<212> TYPE: DNA
<213> ORGANISM: Artificial Sequence
<220> FEATURE:
<223> OTHER INFORMATION: Primer Sequence

<400> SEQUENCE: 13
cagtgttgga ccttggaatg atg                                          23

<210> SEQ ID NO 14
```

```
<211> LENGTH: 35
<212> TYPE: DNA
<213> ORGANISM: Artificial Sequence
<220> FEATURE:
<223> OTHER INFORMATION: Primer Sequence

<400> SEQUENCE: 14
gcaagcttgg cgcgccggga tcgaagaaat gatgg                              35

<210> SEQ ID NO 15
<211> LENGTH: 35
<212> TYPE: DNA
<213> ORGANISM: Artificial Sequence
<220> FEATURE:
<223> OTHER INFORMATION: Primer Sequence

<400> SEQUENCE: 15
cgcgcgcgct gcaggtgtgg aagaacgatt acaac                              35

<210> SEQ ID NO 16
<211> LENGTH: 31
<212> TYPE: DNA
<213> ORGANISM: Artificial Sequence
<220> FEATURE:
<223> OTHER INFORMATION: Primer Sequence

<400> SEQUENCE: 16
gcctgcagtc taactgatct atccaaaact g                                  31

<210> SEQ ID NO 17
<211> LENGTH: 34
<212> TYPE: DNA
<213> ORGANISM: Artificial Sequence
<220> FEATURE:
<223> OTHER INFORMATION: Primer Sequence

<400> SEQUENCE: 17
cgtgagctcc gtacgtaacg aacgcagaat tttc                               34

<210> SEQ ID NO 18
<211> LENGTH: 58
<212> TYPE: DNA
<213> ORGANISM: Artificial Sequence
<220> FEATURE:
<223> OTHER INFORMATION: Primer Sequence

<400> SEQUENCE: 18 tttttaatt ttaatcaaaa aaggatcccc gggctgcaat gtcatttcaa ttgaaacg      58

<210> SEQ ID NO 19
<211> LENGTH: 55
<212> TYPE: DNA
<213> ORGANISM: Artificial Sequence
<220> FEATURE:
<223> OTHER INFORMATION: Primer Sequence

<400> SEQUENCE: 19
ccaccaccag tagagacatg ggagatctag aattccttta agtacgaacc gttgg        55

<210> SEQ ID NO 20
<211> LENGTH: 17
<212> TYPE: DNA
<213> ORGANISM: Artificial Sequence
<220> FEATURE:
<223> OTHER INFORMATION: Primer Sequence

<400> SEQUENCE: 20
```

```
gcgattggca ttatcac                                              17

<210> SEQ ID NO 21
<211> LENGTH: 18
<212> TYPE: DNA
<213> ORGANISM: Artificial Sequence
<220> FEATURE:
<223> OTHER INFORMATION: Primer Sequence

<400> SEQUENCE: 21
gcagctttaa ataatcgg                                             18

<210> SEQ ID NO 22
<211> LENGTH: 30
<212> TYPE: DNA
<213> ORGANISM: Artificial Sequence
<220> FEATURE:
<223> OTHER INFORMATION: Primer Sequence

<400> SEQUENCE: 22
atctgtcgac gacatagaaa tatcgaatgg                                30

<210> SEQ ID NO 23
<211> LENGTH: 27
<212> TYPE: DNA
<213> ORGANISM: Artificial Sequence
<220> FEATURE:
<223> OTHER INFORMATION: Primer Sequence

<400> SEQUENCE: 23
atctgtcgac aggaacaatt tcgggcc                                   27

<210> SEQ ID NO 24
<211> LENGTH: 31
<212> TYPE: DNA
<213> ORGANISM: Artificial Sequence
<220> FEATURE:
<223> OTHER INFORMATION: Primer Sequence

<400> SEQUENCE: 24
atctgtcgac gaacatagaa atatcgaatg g                              31

<210> SEQ ID NO 25
<211> LENGTH: 27
<212> TYPE: DNA
<213> ORGANISM: Artificial Sequence
<220> FEATURE:
<223> OTHER INFORMATION: Primer Sequence

<400> SEQUENCE: 25
atctgtcgac aggaacaatt tcgggcc                                   27

<210> SEQ ID NO 26
<211> LENGTH: 18
<212> TYPE: DNA
<213> ORGANISM: Artificial Sequence
<220> FEATURE:
<223> OTHER INFORMATION: Primer Sequence

<400> SEQUENCE: 26
tagacgaaga taggaatc                                             18

<210> SEQ ID NO 27
<211> LENGTH: 20
<212> TYPE: DNA
<213> ORGANISM: Artificial Sequence
<220> FEATURE:
```

<223> OTHER INFORMATION: Primer Sequence

<400> SEQUENCE: 27
gtttatcatt atcaatactc                                         20

<210> SEQ ID NO 28
<211> LENGTH: 20
<212> TYPE: DNA
<213> ORGANISM: Artificial Sequence
<220> FEATURE:
<223> OTHER INFORMATION: Primer Sequence

<400> SEQUENCE: 28
catcaagaac aaacaagctc                                         20

<210> SEQ ID NO 29
<211> LENGTH: 18
<212> TYPE: DNA
<213> ORGANISM: Artificial Sequence
<220> FEATURE:
<223> OTHER INFORMATION: Primer Sequence

<400> SEQUENCE: 29
cgttggttct tcagttcc                                           18

<210> SEQ ID NO 30
<211> LENGTH: 19
<212> TYPE: DNA
<213> ORGANISM: Artificial Sequence
<220> FEATURE:
<223> OTHER INFORMATION: Primer Sequence

<400> SEQUENCE: 30
gccttctatt aagttgaac                                          19

<210> SEQ ID NO 31
<211> LENGTH: 31
<212> TYPE: DNA
<213> ORGANISM: Artificial Sequence
<220> FEATURE:
<223> OTHER INFORMATION: Primer Sequence

<400> SEQUENCE: 31
atctgtcgac gaacatagaa atatcgaatg g                            31

<210> SEQ ID NO 32
<211> LENGTH: 27
<212> TYPE: DNA
<213> ORGANISM: Artificial Sequence
<220> FEATURE:
<223> OTHER INFORMATION: Primer Sequence

<400> SEQUENCE: 32
atctgtcgac aggaacaatt tcgggcc                                 27

<210> SEQ ID NO 33
<211> LENGTH: 47
<212> TYPE: DNA
<213> ORGANISM: Artificial Sequence
<220> FEATURE:
<223> OTHER INFORMATION: Primer Sequence

<400> SEQUENCE: 33
cttagcgatt ggcattatca cataatgatt gctgaagctt cgtacgc           47

<210> SEQ ID NO 34

```
<211> LENGTH: 45
<212> TYPE: DNA
<213> ORGANISM: Artificial Sequence
<220> FEATURE:
<223> OTHER INFORMATION: Primer Sequence

<400> SEQUENCE: 34
tgacacgtat agaatgatgc attaccttgt ccggcagatc cgcgg              45
```

SACCHAROMYCES STRAIN WITH ABILITY TO GROW ON PENTOSE SUGARS UNDER ANAEROBIC CULTIVATION CONDITIONS

This application is a National Stage Application of PCT/SE2009/000498, filed 20 Nov. 2009, which claims benefit of Serial No. 0802467-1, filed 24 Nov. 2008 in Sweden and which applications are incorporated herein by reference. To the extent appropriate, a claim of priority is made to each of the above disclosed applications.

FIELD OF INVENTION

The invention relates to an improved *Saccharomyces* strain displaying improved viability and growth during anaerobic fermentation of pentose carbon sources such as xylose and producing fermentation products such as ethanol.

BACKGROUND OF INVENTION

Bioethanol production from renewable feedstock by baker's yeast *Saccharomyces cerevisiae* has become an attractive alternative to fossil fuels. However, the availability of starch or sucrose based feedstock such as corn grain or sugar cane is expected to be insufficient to cover future worldwide needs for bioethanol (Gray et al., 2006. Bioethanol. Current Opinion Chemical Biology. 10(2):141-146). A foreseen solution is the utilization of lignocellulosic feedstocks, such as corn stover, wheat straw, sugar cane bagasse, wood, etc (Hahn-Hägerdal et al., 2006. Bioethanol—the fuel of tomorrow from the residues of today. Trends Biotechnol. 24(12):549-556). This requires overcoming new challenges associated with the utilization of these complex raw materials.

A substantial fraction of lignocellulosic material consists of pentoses, xylose and arabinose that need to be efficiently converted to make the bioethanol process cost-effective. *Saccharomyces* species cannot ferment these pentoses as such and need to be modified to be able to do that. However, attempts have been made to modify *Saccharomyces* strains to produce ethanol and other fermentation products such as butanol, lactate, 1,4-diacids (succinate, fumaric, malic), glycerol, sorbitol, mannitol, xylitol/arabinitol, L-ascorbic acid, xylitol, hydrogen gas, 2,5-furan dicarboxylic acid, 3-hydroxy propionic acid, aspartic acid, glutaric acid, glutamic acid, itaconic acid, levulinic acid, and 3-hydroxybutyrolactone in an efficient way. *Saccharomyces cerevisiae*, which can be grown on xylose aerobically and which ferments xylose to ethanol has been obtained, wherein said strain either has genes from the *Pichia stipitis* xylose pathway or heterologous xylose isomerase (XI) genes and overexpresses the endogenous xylulose kinase gene (Hahn-Hägerdal B, Karhumaa K, Fonseca C, Spencer-Martins I, Gorwa-Grauslund M F (2007). Such strains do not grow anaerobically on xylose as sole carbon source. However, anaerobic growth is a crucial trait for industrial fermentation processes since it renders the yeast viability and viability is directly related to the ability of the yeast to ferment efficiently. Anaerobic xylose growth by recombinant strains of *S. cerevisiae* has been achieved in haploid laboratory strains by random evolutionary engineering strategies (Sonderegger M, Sauer U (2003) Evolutionary engineering of *Saccharomyces cerevisiae* for anaerobic growth on xylose. Appl Environ Microbiol 69:1990-8; Kuyper et al (2004) Minimal metabolic engineering of *Saccharomyces cerevisiae* for efficient anaerobic xylose fermentation: a proof of principle. FEMS Yeast Res 4:655-64). Traits obtained via random strategies are not easily identified, and therefore such traits are difficult to transfer to other strains. Moreover laboratory strains do not ferment toxic lignocellulose hydrolysates (Karhumaa K, Garcia Sanchez R, Hahn-Hägerdal B, Gorwa-Grauslund M F (2007) Comparison of the xylose reductase-xylitol dehydrogenase and the xylose isomerase pathways for xylose fermentation by recombinant *Saccharomyces cerevisiae*. Microb Cell Fact 6:5).

Furthermore, when applied to polyploid and aneuploid industrial strains random strategies often result in limited improvements. Therefore there is still a need to design well-defined rational metabolic engineering strategies/technologies, which convey traits that provide *Saccharomyces* sp. strains with the ability to grow and ferment pentose sugars anaerobically and which can be transferred to any other polyploid and aneuploid *Saccharomyces* sp. strain.

SUMMARY OF THE INVENTION

The invention relates to a method as well as to new *Saccharomyces* species strains with improved viability obtained by rational metabolic engineering technology that grow on pentose sugars as sole carbon sources under anaerobic conditions and that produce ethanol and other fermentation products such as butanol, lactate, 1,4-diacids (succinate, fumaric, malic), glycerol, sorbitol, mannitol, xylitol/arabinitol, L-ascorbic acid, xylitol, hydrogen gas, 2,5-furan dicarboxylic acid, 3-hydroxy propionic acid, aspartic acid, glutaric acid, glutamic acid, itaconic acid, levulinic acid, and 3-hydroxybutyrolactone and cell mass. The fact that the novel strains are obtained by rational metabolic engineering technology and lack genes expressed from multicopy plasmids, make it possible to specifically transfer the traits to any industrial polyploid and aneuploid strains.

The invention relates to a *Saccharomyces* sp. strain, being viable and able to grow on pentose sugars under anaerobic fermentation and comprising in the genome a xylose reductase (XR) gene having NADH-preference, wherein said gene is expressed by a constitutive promoter and increased expression of the xylitol dehydrogenase (XDH).

By using constitutive promoters or parts thereof, such as truncated versions thereof such as those of TDH3, HXT7, TEF1 and PGK1 genes for XR expression and by modifying the *P. stipitis* XR coenzyme preference by site-directed mutagenesis, i.e., towards NADH-preference it was for the first time possible to obtain both cell growth and ethanolic fermentation under anaerobic conditions using penstose sugars such as xylose as the sole carbon source.

By this invention *Saccharomyces* is forced towards NADH preference in the xylose to xylitol conversion by XR as well as a higher constitutive flux through the XR, which results in growth without air and oxygen in medium comprising pentose sugars as sole carbon sources, higher production of ethanol and other fermentation products such as butanol, lactate, 1,4-diacids (succinate, fumaric, malic), glycerol, sorbitol, mannitol, xylitol/arabinitol, L-ascorbic acid, xylitol, hydrogen gas, 2,5-furan dicarboxylic acid, 3-hydroxy propionic acid, aspartic acid, glutaric acid, glutamic acid, itaconic acid, levulinic acid, and 3-hydroxybutyrolactoneand and less by-product formation.

In a second aspect the invention relates to a method of producing ethanol/cellmass and other fermentation products comprising the steps of providing a medium comprising xylose and a *Saccharomyces* sp strain as defined above, adding said medium and strain to a fermentation reactor, performing fermentation with said strain under anaerobic conditions and utilising the carbon source xylose and producing ethanol and other fermentation products such as butanol, lactate, 1,4-diacids (succinate, fumaric, malic), glycerol, sorbitol, mannitol, xylitol/arabinitol, L-ascorbic acid, xylitol, hydrogen gas, 2,5-furan dicarboxylic acid, 3-hydroxy propionic acid, aspartic acid, glutaric acid, glutamic acid, itaconic acid, levulinic acid, and 3-hydroxybutyrolactone.

In a third aspect the invention relates to the use of the invented strains as well as the method disclosed herein.

BRIEF DESCRIPTION OF THE DRAWINGS

FIG. 6A. Sugar consumption and product formation of the anaerobic batch fermentations on defined medium with 20 g/l xylose for the strains. A) Control-PPP-XYL, B) PGM2-PPP-XYL Symbols: (□) xylose, (▲) ethanol, (○) biomass (DW), (+) acetate, (x) glycerol, (−) xylitol FIG. 6B. Anaerobic growth on batch fermentation on defined medium with 20 g/l xylose for the strains (△) Control-PPP-XYL and (■) PGM2-PPP-XYL.

DETAILED DESCRIPTION OF THE INVENTION

Definitions

Figure 1:
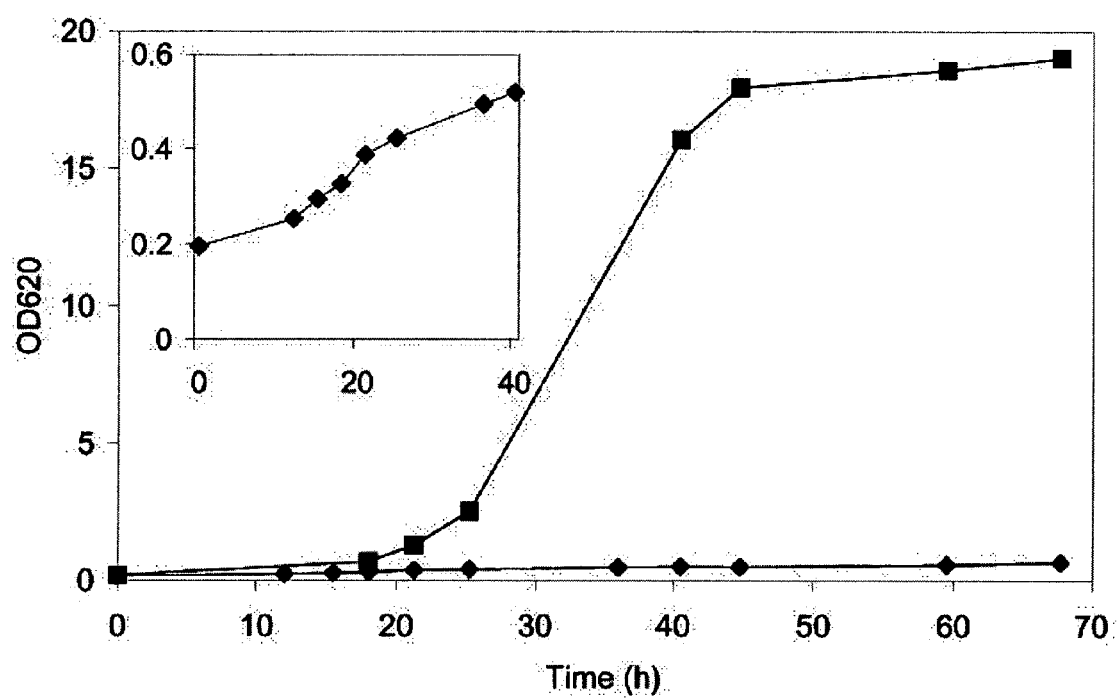
FIG. 1. Aerobic growth of S. cerevisiae strain TMB3321 (♦) with the ADH1 promoter regulating XR expression and strain TMB3325 (■) with the TDH3 promoter regulating XR expression in YNB medium containing 50 g $l^{-1}$ xylose. Growth of TMB3321 is shown with a different scale in the subfigure.

In the context of the present application and invention the following definitions apply:

The term "analogue thereof" is intended to mean that part of or the entire polypeptide of a polypeptide is based on non protein amino acid residues, such as aminoisobutyric acid (Aib), norvaline gamma-aminobutyric acid (Abu) or ornithine. Examples of other non protein amino acid residues can be found at www<.>hort<.>purdue<.>edu/rhodcv/hort640c/polyam/po00008<.>htm.

In the present context, amino acid names and atom names are used as defined by the Protein DataBank (PNB) (www<.>pdb<.>org), which is based on the IUPAC nomenclature (IUPAC Nomenclature and Symbolism for Amino Acids and Pep-tides (residue names, atom names etc.), Eur J. Biochem., 138, 9-37 (1984) together with their corrections in Eur J. Biochem., 152, 1 (1985). The term "amino acid" is intended to indicate an amino acid from the group consisting of alanine (Ala or A), cysteine (Cys or C), aspartic acid (Asp or D), glutamic acid (Glu or E), phenyl-alanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W) and tyrosine (Tyr or Y), or derivatives thereof.

The terminology used for identifying amino acid positions is illustrated as follows: K270 indicates that the position 270 is occupied by a Lysine residue in the amino acid sequence encoded by the sequence shown in SEQ ID NO:1. K270R indicates that the Lysine residue of position 270 has been substituted with an Arginine residue.

The term "overexpression/overexpressing" includes that the gene may be upregulated as well as overexpressed. This includes that the endogenous gene may be upregulated as well as a new copy of the gene may be integrated into the strain, optionally into the genome under control of a promoter wherein the promoter optionally can be a constitutive promoter.

The term "rational metabolic engineering" is intended to mean the targeted manipulation of a gene leading to among others higher or lower expression, deletion, site-directed change of nucleotide sequence such that its biological activity is altered. In contrast to random strain development methods such as mutagenesis, evolutionary engineering and cross breeding, rational metabolic engineering therefore is transferable and can be repeated in any strain of choice, including industrial polyploidy and aneuploid isolates. Thus rational metabolic engineering is intended to mean a strain engineering approach in which the resulting strain has only been subjected to modifications whose outcome in terms of genetic features can be known a priori. In addition, a rationally engineered strain is expected to have acquired only genetic features known in terms of their sequence, purposefully inserted in the form of plasmids and/or DNA fragments of known sequence yet not necessarily in terms of number of times this particular sequence is present in the new strain.

Invention

The invention relates to a method as well as to new Saccharomyces species strains with improved viability obtained by rational metabolic engineering technology, wherein said strain grow on pentose sugars as sole carbon sources under anaerobic conditions and produce ethanol and other fermentation products The invention relates to a Saccharomyces sp. strain, being viable and grow on pentose sugars under anaerobic fermentation comprising in the genome a xylose reductase gene having NADH-preference, wherein said gene is expressed by a constitutive promoter and increased expression of the xylitol dehydrogenase (XDH). One example being that said xylose reductase gene is derived from Pichia stipitis and has the substitution K270R(XRK270R). Another example being that said xylose reductase gene is derived from Pichia stipitis and has the substitution N272D and P275Q in combination (XRN272DP275Q) or separately (XRN272D; XRP275Q).

By the development of such a new strain it is for the first time possible to have a viable strain that can grow under anaerobic conditions using solely pentose as the sugar, such as xylose and still produce high amounts of ethanol and thereby be able to use the strain for commercial purposes in fermentation for the production of for example bioethanol from pentose and hexose carbon sources.

In another embodiment the strain may also have increased level of phosphoglucomutase obtained for instance by expression of PGM2 gene with a constitutive promoter, such as those mentioned above and thereby be able to produce ethanol with higher productivity.

As an alternative may a functional equivalent derivative of any of the mentioned genes within the application be used. The term functionally equivalent derivative includes a protein with catalytic activity for the conversion of a pentose sugar into the corresponding sugar alcohol by means of NADH oxidation or a protein with catalytic activity for the conversion of glucose-1-phosphate to glucose-6-phosphate.

The invented strain(s) will allow the production of fermentation products including ethanol and cell mass under anaerobic conditions on xylose. Anaerobic growth increases cell viability and permits cell recirculation, thus saving carbon for ethanol and fermentation products production. It increases the production of ethanol and fermentation product and improves the overall process economics.

The invented strain may also overexpress the genes involved in the non-oxidative pentose phosphate pathway (PPP) overexpression of the genes transaldolase (TAL1), transketolase (TKL1), ribose 5-phosphate ketol-isomerase (RKI1) and ribulose 5-phosphate epimerase (RPE1). By combining the genomic integrated overexpression of XR with NADH preference (XRK270R or XRN272DP275Q or XRN272D or XRP275Q and/or PGM2 under a constitutive promoter and the non-oxidative PPP the xylose utilisation will be increased compared to when the different modifications are used alone.

The Saccharomyces sp. strain according the description above may also overexpress other genes such as the gene xylulokinase (XK). This will further increase the production of ethanol and other fermentation products such as ethanol, butanol, lactate, 1,4-diacids (succinate, fumaric, malic), glycerol, sorbitol, mannitol, xylitol/arabinitol, L-ascorbic acid, xylitol, hydrogen gas, 2,5-furan dicarboxylic acid, 3-hydroxy propionic acid, aspartic acid, glutaric acid, glutamic acid, itaconic acid, levulinic acid, and 3-hydroxybutyrolactone.

The genes of interest to be introduced/transformed into the Saccharomyces sp. strain may be expressed by a constitutive promoter which will result in that the xylose will continuously be utilised and that the rate of fermentation product formation including ethanol production is high. Examples of promoters are sequences based on promoters for the enzymes/proteins, glyceraldehyde-3-phosphate dehydrogenase, isozyme 3 (TDH3 or YGR192C); a truncated version of the high-affinity glucose transporter of the major facilitator superfamily (HXT7 or YDR342C); 3-phosphoglycerate kinase (PGK1 or YCR012W); and translational elongation factor EF-1 alpha (TEF1 or YPR080W). One example being that the TDH3 promoter is used to express the XRK270R gene and a truncated HXT7 promoter is used to express the PGM2 gene, wherein all genes are stably integrated into the genome of the Saccharomyces sp. strain, thus enabling straight transfer of improved traits to industrial polyploid and aneuploid strains. The promoters may be the complete promoter as ell as parts thereof. The nucleotide sequences showing the TDH3 linked to the XRK270R gene being shown in SEQ ID NO:1 and the nucleotide sequence showing HXT7 linked to the PGM2 gene being shown in SEQ ID NO:2.

The strain of the invention may be selected from the group consisting of Saccharomyces cerevisiae, Saccharomyces bayanus and Saccharomyces carlsbergensis. For example the strain may be Saccharomyces cerevisiae which is used in the EXAMPLES. Other examples of strains are the S. cerevisiae strains DBY746, AH22, S150-2B, GPY55-15Bα, CEN.PK, TMB3500, VTT-A-63015, VTT-A-85068, VTT-c-79093) and their derivatives as well as Saccharomyces sp. 1400, 424A (LNH-ST), 259A (LNH-ST) in addition to any polyploid and aneuploid industrial Saccharomyces isolate found suitable for ethanol production from xylose.

The invented strains have improved properties compared to the wild-type original strains, i.e., consuming a higher amount of xylose faster and producing a higher amount of fermentation products such as ethanol faster. Example on how to determine the improved properties are shown in the EXAMPLES below.

The invention also relates to a method of producing cell mass and fermentation products such as ethanol, butanol, lactate, 1,4-diacids (succinate, fumaric, malic), glycerol, sorbitol, mannitol, xylitol/arabinitol, L-ascorbic acid, xylitol, hydrogen gas, 2,5-furan dicarboxylic acid, 3-hydroxy propionic acid, aspartic acid, glutaric acid, glutamic acid, itaconic acid, levulinic acid, and 3-hydroxybutyrolactone comprising the steps of: providing a medium containing xylose and a Saccharomyces sp strain as defined above, adding said medium and strain to a fermentation reactor and performing fermentation with said strain under anaerobic conditions and utilising the carbon source xylose and producing ethanol. The fermentation may be performed without addition of air, oxygen, and/or nitrogen, with carbon dioxide produced during fermentation generating an anaerobic atmosphere. The method may be a fermentation method, either a batch fed-batch, continuous or continuous fermentation with cell recirculation. The method may use xylose as the sole carbon source or mixtures of carbon sources such as glucose, mannose, galactose, xylose and arabinose. The amount of the different carbon sources depends on the raw material used, where soft woods generally contain higher amounts of the hexose sugars glucose, mannose and galactose, whereas hardwoods and agricultural crops contain higher amounts of the pentose sugars xylose and arabinose. The fermentation may take place at a temperature in the range of about 30-45° C., such as 31, 32, 33, 34, 35, 36, 37, 38, 39° C., 40° C., 41° C., 42° C., 43° C., 44° C. or 45° C. and an acidic pH, such as 6-3. The ethanol yield in the invented method using said invented Saccharomyces sp strains will be from about 0.35 g/g carbon source. Examples of yields are 0.35, 0.40, 0.45, up to 0.5 g/g sugar. The rate of ethanol production may be at least 0.1 g/g biomass/h increasing to 0.6 g/g biomass/h. The xylose consumption rates may be at least 0.28 g/g biomass/h increasing to at least 1 g/g biomass/hour.

Finally the invention relates to the use of Saccharomyces sp strains for the production of ethanol and other fermentation products as defined above.

Following examples are intended to illustrate, but not to limit, the invention in any manner, shape, or form, either explicitly or implicitly.

EXAMPLES

Example 1

The co-consuming xylose and arabinose Saccharomyces cerevisiae TMB 3061 (Karhumaa, Wiedemann et al. 2006) was subjected to an evolutionary engineering approach in order to increase the uptake of pentose sugars. In the resulting strain TMB3130, it was observed that the fermentation product distribution and notably the XR-driven arabitol production was greatly affected by the carbon source used for inoculum preparation (Garcia Sanchez R., Karhumaa et al. Submitted).

The xylose and arabinose consuming *S. cerevisiae* strain TMB 3130 is derived from strain TMB3400 that utilizes the ADH1 promoter to control the expression of the *Pichia stipitis* XYL1 gene that encodes XR (Wahlbom, van Zyl et al. 2003; Garcia Sanchez R., Karhumaa et al. Submitted). The ADH1 promoter has been a common choice for driving heterologous gene expression in *S. cerevisiae* (Ammerer 1983; Mumberg, Muller et al. 1995). Still, it was investigated whether the change in by-product distribution was caused by differences in XR activity.

Crude extracts were prepared from TMB 3130 cells grown in defined medium supplemented with 20 g/l glucose, 20 g/l xylose, 20 g/l arabinose or the mixture of 20 g/l xylose and 20 g/l arabinose and the XR and XDH activities were measured. In practice, cells grown overnight on YNB medium with glucose were used to inoculate shake flask cultures with different carbon sources: 20 g/L xylose, 20 g/L arabinose, 20 g/L glucose, or a mixture of 20 g/L xylose and 20 g/L arabinose. Next, cells were harvested in exponential phase and washed twice with water. Y-PER reagent (Pierce Biotechnology, Rockford, Ill., USA) was used to extract proteins. The protein concentration was determined with the Coomassie Plus protein assay reagent (Pierce, Rockford, Ill., USA) with bovine serum albumine as standard. XR activity was measured as previously described (Smiley and Bolen 1982; Eliasson, Christensson et al. 2000). XDH activity was adapted as previously reported (Rizzi M 1989) except using triethanolamine buffer at pH 7 (Wahlbom, van Zyl et al. 2003). The experiments were performed in biological triplicates and duplicate measurements with different dilutions of the extracted proteins. All assays were performed with an Ultrospec 2100 pro spectrophotometer (Amersham Biosciences, Uppsala, Sweden).

Glucose grown cells displayed a specific XR activity of $0.72 \pm 0.06$ U (mg protein)$^{-1}$, while the xylose and arabinose grown cells displayed considerably lower activities, $0.05 \pm 0.01$ U (mg protein)$^{-1}$ and $0.13 \pm 0.02$ U (mg protein)$^{-1}$, respectively or $0.07 \pm 0.04$ U (mg protein)$^{-1}$ on cells grown on the mixture of arabinose and xylose (Table 1).

The results presented for strain TMB 3130 suggest that the ADH1 promoter is not highly activated by pentose sugars. In contrast, the xylitol dehydrogenase (XDH) activity which is controlled by the PGK1 promoter in this strain was more similar for all three sugar media or in the medium with a mixture of xylose and arabinose (Table 1). In light of these results, we conclude that the ADH1 promoter is not the most appropriate to use when engineering *S. cerevisiae* for pentose fermentation whereas PGK1 promoter is a suitable promoter. The ADH1 promoter is not strongly activated when *S. cerevisiae* is grown on pentose sugars.

TABLE 1

XR and XDH activity U/mg protein of crude protein extracts from strain TMB 3130 grown in defined medium with different carbon sources (20 g/L each).

| Strain | Carbon source | XR activity U/mg protein | XDH activity U/mg protein |
|---|---|---|---|
| TMB 3130 | Glucose | 0.72 ± 0.06 | 1.85 ± 0.61 |
| | Xylose | 0.05 ± 0.01 | 0.89 ± 0.05 |
| | Arabinose | 0.13 ± 0.02 | 0.46 ± 0.12 |
| | arabinose and xylose | 0.07 ± 0.04 | 1.18 ± 0.23 |

Ammerer, G. (1983). "Expression of Genes in Yeast Using the Adci Promoter." *Methods in Enzymology* 101: 192-201.

Eliasson, A., C. Christensson, et al. (2000). "Anaerobic xylose fermentation by recombinant *Saccharomyces cerevisiae* carrying XYL1, XYL2, and XKS1 in mineral medium chemostat cultures." *Appl Environ Microbiol* 66(8): 3381-6.

Garcia Sanchez R., K. Karhumaa, et al. (Submitted). "Evolutionary engineering of a D-xylose and L-arabinose co-utilizing industrial and recombinant *Saccharomyces cerevisiae* strain."

Karhumaa, K., B. Wiedemann, et al. (2006). "Co-utilization of L-arabinose and D-xylose by laboratory and industrial *Saccharomyces cerevisiae* strains." *Microb Cell Fact* 5: 18.

Mumberg, D., R. Muller, et al. (1995). "Yeast vectors for the controlled expression of heterologous proteins in different genetic backgrounds." *Gene* 156(1): 119-22.

Rizzi M, H. K., Erlemann P, Bui-Thahn N A, Dellweg H (1989). "Purification and properties of the NAD+-xylitol-dehydrogenase from the yeast *Pichia stipitis*." *J Ferment Bioeng* 67: 20-24.

Smiley, K. L. and P. L. Bolen (1982). "Demonstration of D-xylose reductase and D-xylitol dehydrogenase in *Pachysolen tannophilus*." *Biotech Lett* 4: 607-610.

Wahlbom, C. F., W. H. van Zyl, et al. (2003). "Generation of the improved recombinant xylose-utilizing *Saccharomyces cerevisiae* TMB 3400 by random mutagenesis and physiological comparison with *Pichia stipitis* CBS 6054." *FEMS Yeast Res* 3(3): 319-26.

Example 2

*S. cerevisiae* strains expressing XR under ADH1 and TDH3 promoters were constructed and evaluated for growth on xylose.

Strain Construction

Plasmids and strains used in the construction are summarized in Table 2. A DNA cassette containing ADH1p-XYL1-ADH1t PGK1p-XYL2-PGK1t was inserted into YIplac211 (Gietz and Sugino, 1988) creating YIpOB2. The XYL1 gene was removed from YIpOB2 by digestion with XbaI and self-ligation to create YIpOB3. Restriction endonuclease recognition sites in primer sequences are indicated by underlined and italic letters. The glyceraldehyde-3-phosphate dehydrogenase isozyme 3 (TDH3) promoter was amplified from the vector p426GPD using primers containing restriction sites HindIII, AscI (5'-GCATAAGCTTGGCGCGCCAG TTTAT-CATTATCAATACTCGCCATTTC-3' (SEQ. ID. NO. 6)) and XbaI (5'-GCATTCTAGAATCCGTCGAAACTAAGTTC-3' (SEQ. ID. NO. 7)). The plasmid YIpOB7 was created by replacing the alcohol dehydrogenase isozyme 1 (ADH1) promoter in plasmid YIpOB3 with the TDH3 promoter PCR product using restriction sites HindIII and XbaI. The *Pichia stipitis* XYL1 gene fragment was excised from plasmid YIpOB2 and inserted into YIpOB7 using the XbaI restriction sites creating plasmid YIpOB8. The constructed plasmids were analyzed with restriction analysis and PCR to confirm correct insertions. The inserted parts were sequenced to verify that no mutations were introduced. YIpOB2 was cleaved with restriction enzyme ApaI within the URA3 gene and transformed into strain TMB 3044 (Karhumaa et al., 2005), resulting in strain TMB 3321. Plasmid YIpOB8 was cleaved with restriction enzyme Eco32I within the URA3 gene and transformed into strain TMB3044 (Karhumaa et al., 2005), resulting in strain TMB3325.

TABLE 2

Plasmids and strains used in EXAMPLE 2

| Plasmid | Features | Reference |
|---|---|---|
| p426GPD | LEU2, TDH3p, CYC7t | (Mumberg et al. 1995) |
| YIplac211 | URA3 | (Gietz and Sugino 1988) |
| YIpOB2 | ADH1p-XYL1-ADH1t, PGK1p-XYL2-PGK1t, URA3 | This work |
| YIpOB3 | ADH1p-ADH1t, PGK1p-XYL2-PGK1t, URA3 | This work |
| YIpOB7 | TDH3p-ADH1t, PGK1p-XYL2-PGK1t, URA3 | This work |
| YIpOB8 | TDH3p-XYL1-ADH1t, PGK1p-XYL2-PGK1t, URA3 | This work |

| S. cerevisiae strain | Genotype | Reference |
|---|---|---|
| TMB3044 | CEN.PK 2-1C, MATa, ura3-52, Δgre3, his3::HIS3 PGK1p-XKS1-PGK1t, TAL1::PGK1p-TAL1-PGK1t, TKL1::PGK1p-TKL1-PGK1t, RKI1::PGK1p-RKI1-PGK1t, RPE1::PGK1p-RPE1-PGK1t | (Karhumaa et al. 2005) |
| TMB3321 | TMB3044, ura3::URA3 YIpOB2 | This work |
| TMB3325 | TMB3044, ura3::URA3 YIpOB8 | This work |

Growth Rate

Yeast cultures were inoculated with cells washed with sterile H$_2$O to an optical density at 620 nm (OD$_{620}$) of 0.2. S. cerevisiae strains TMB3321 and TMB3325 were grown aerobically in 500 ml baffled flasks containing 50 ml YNB medium, buffered to pH 5.5 with 50 mM potassium hydrogen phthalate, supplemented with 50 g l$^{-1}$ xylose and 13.4 g l$^{-1}$ YNB at 30° C. and 200 rpm. Each strain was cultivated in biological triplicates. Growth was determined by measuring OD620 with a Hitachi U-1800 Spectrophotometer (Hitachi Ltd., Tokyo, Japan).

Strain TMB3325, harbouring the constitutive TDH3 promoter, grew aerobically on xylose at a stable exponential growth rate of 0.18±0.01 h$^{-1}$ (FIG. 1). In contrast, strain TMB3321, harbouring the ADH1 promoter, displayed a growth rate of only 0.04±0.02 h$^{-1}$. The growth of TMB3321 decreased after 24 hours and thereafter it displayed slower non-exponential growth (FIG. 1, subfigure).

References

Gietz, R. D. and Sugino, A. (1988). New yeast-*Escherichia coli* shuttle vectors constructed with in vitro mutagenized yeast genes lacking six-base pair restriction sites. Gene 74, 527-534.

Karhumaa et al. (2005). Investigation of limiting metabolic steps in the utilization of xylose by recombinant *Saccharomyces cerevisiae* using metabolic engineering. Yeast. 22(5):359-368.

Mumberg, et al. (1995). Yeast vectors for the controlled expression of heterologous proteins in different genetic backgrounds. Gene 156:119-22.

Example 3

A reporter strain for the evaluation of TDH3 promoter on different carbon sources was constructed and tested on glucose and xylose.

Strain Construction

Restriction endonuclease recognition sites in primer sequences are indicated by underlined or italic letters. The *E. coli* LacZ gene was amplified by whole-cell PCR from strain BL21-DE3 (Stratagene, La Jolla, Calif., USA) with primers containing restriction sites for HindIII (5'-GCGC AAGCTTATGACCATGATTACGGATT-3' (SEQ. ID. NO. 8)) and SalI (5'-GTGAGTCGACTTATTTTTGACACCA-GACC-3' (SEQ. ID. NO. 9)). The PCR product was inserted into the vector p426GPD (Mumberg et al., 2005) creating plasmid p426lac (Table 3). Plasmid YIpOB1 (Table 3) was integrated into strain TMB3043 (Karhumaa et al., 2005) resulting in strain TMB3320 (Table 3). TMB3320 was transformed with plasmid p426lac resulting in strain TMB3095. Strain TMB3095 is able to grow on xylose as a sole carbon source and the expression of TDH3 promoter can be measured as beta-galactosidase activity.

Reporter Gene Activity Measurement During Aerobic Growth on Xylose or Glucose

S. cerevisiae strain TMB3095, able to grow on xylose as a sole carbon source and expressing LacZ reporter gene controlled by TDH3 promoter, was grown in 1 l baffled flasks containing 0.1 l YNB medium supplemented with 50 g l$^{-1}$ xylose and 13.4 g l$^{-1}$ YNB or 20 g l$^{-1}$ glucose and 6.7 g l$^{-1}$ YNB. Crude cell extracts were prepared from cells harvested in exponential growth phase with Yeast Protein Extraction Reagent (Y-PER) (PIERCE, Rockford, Ill., USA) according to the manufacturer's instructions. Crude protein extracts were used for beta-galactosidase activity measurements as previously described (Rupp, 2002). One unit of beta-galactosidase is defined as the amount of enzyme needed to hydrolyze one nmol of 2-nitrophenyl beta-D-galactopyranoside per minute.

Figure 2:
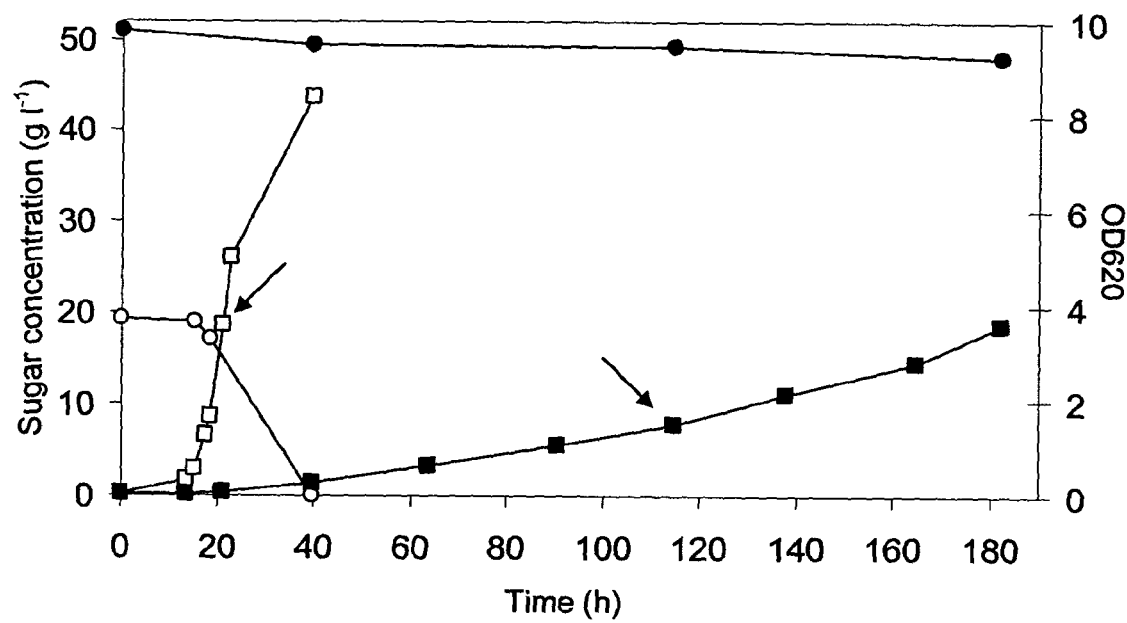
FIG. 2. Cell growth and substrate consumption by strain TMB3095 in YNB medium containing 20 g $l^{-1}$ glucose or 50 g $l^{-1}$ xylose. The sampling points for beta-galactosidase activity measurement are indicated by arrows. ○: Glucose (g $l^{-1}$); ●: Xylose (g $l^{-1}$); □: OD620, glucose culture; ■: OD620, xylose culture FIG. 3. Time course of anaerobic batch fermentation of 20 g $l^{-1}$ glucose and 50 g $l^{-1}$ xylose with strains Y-PsNative (A); Y-PsK270M (B); and Y-PsK270R (C). Symbols: ■ xylose, □ glucose, ▲ ethanol, △ xylitol, ● glycerol, ○ acetate.

TMB3095 was grown aerobically in YNB medium containing 20 g l$^{-1}$ glucose or 50 g l$^{-1}$ xylose (FIG. 2). Beta-galactosidase activity was determined for both conditions in exponential phase (FIG. 2). LacZ expression was essentially identical in glucose and xylose grown cells, with a measured beta-galactosidase specific activity of 501±36 U (mg protein)$^{-1}$ and 498±3 U (mg protein)$^{-1}$, respectively. The TDH3 promoter thus appears to be suitable for constitutive gene expression under growth in different carbon sources.

TABLE 3

Plasmids and strains used in EXAMPLE 3

| Plasmid | Features | Reference |
|---|---|---|
| p426GPD | LEU2, TDH3p, CYC7t | (Mumberg, et al., 1995) |
| p426lac | LEU2, TDH3p-LacZ-CYC7t | This example |
| YIpOB1 | ADH1p-XYL1-ADH1t, PGK1p-XYL2-PGK1t, LEU2 | This example |

| | Genotype | Reference |
|---|---|---|
| *E. coli* strain | | |
| BL21-DE3 | F– dcm ompT hsdS(rB – mB –) gal λ(DE3) | Stratagene, La Jolla, CA, USA |
| *S. cerevisiae* strain | | |
| TMB3043 | CEN.PK 2-1C, MATa, leu2-3 112, ura3-52, Δgre3, his3::HIS3 PGK1p-XKS1-PGK1t, TAL1::PGK1p-TAL1-PGK1t, TKL1::PGK1p-TKL1-PGK1t, RKI1::PGK1p-RKI1-PGK1t, RPE1::PGK1p-RPE1-PGK1t | (Karhumaa, et al., 2005) |
| TMB3320 | TMB3043, leu2::LEU2 YIpOB1, ura3-52 | This example |
| TMB3095 | TMB3320, p426lac | This example |

References

Karhumaa et al. (2005). Investigation of limiting metabolic steps in the utilization of xylose by recombinant *Saccharomyces cerevisiae* using metabolic engineering. Yeast. 22(5):359-368.

Mumberg, et al. (1995). Yeast vectors for the controlled expression of heterologous proteins in different genetic backgrounds. Gene 156:119-22.

Rupp (2002). LacZ assays in yeast-Quantification of β-galactosidase activity in Guthrie, C. and Fink, G. (Eds), Guide to yeast genetics and molecular cell biology, part B, Academic Press, pp. 128-129.

Example 4

Construction of Genetically Modified Strains Carrying Mutated or Native XR

Strains, Plasmids and Medium

*Escherichia coli* strain DH5α (Life Technologies, Rockville, Md., USA) was used for cloning. Plasmids and *S. cerevisiae* strains are summarized in Table 4. All strains were stored in 15% glycerol at −80° C. *E. coli* was grown in LB-medium (Ausubel et al., 1995). Yeast cells from freshly streaked YPD plates (Ausubel et al., 1995) or defined mineral medium plates (Jeppsson et al., 2006) were used for inoculation. Liquid cultures of *S. cerevisiae* were grown in YPD medium (Ausubel et al., 1995) or defined mineral medium (Jeppsson et al., 2006). Defined mineral medium (Jeppsson et al., 2006) supplemented with 0.4 g l$^{-1}$ Tween 80, 0.01 g l$^{-1}$ ergosterol and 0.5 ml l$^{-1}$ antifoam (Dow Corning® Antifoam RD Emulsion, VWR International Ltd, Poole, UK) was used in anaerobic fermentation.

Genetic Techniques

Plasmid DNA was prepared with the GeneJET™ Plasmid Miniprep Kit (Fermentas UAB, Vilnius, Lithuania). Agarose gel DNA extraction was made with QIAquick® Gel Extraction Kit (Qiagen GmbH, Hilden, Germany). Primers from MWG-Biotech AG (Ebersberg, Germany) and Pfu DNA Polymerase and dNTP from Fermentas (Vilnius, Lithuania) were used for polymerase chain reactions (PCR). Primers used are listed in Table 2. PCR amplification was performed in a GeneAmp PCR system 9700 (Applied Biosystems, Foster City, Calif., USA). PCR product purification was made with the E.Z.N.A.® Cycle-Pure Kit (Omega Bio-tek Inc, Doraville, Ga., USA). BigDye® Terminator v1.1 Cycle Sequencing Kit (Applied Biosystems) was used for DNA sequencing reactions. Sequencing was performed by BM labbet AB (Furulund, Sweden). Restriction endonucleases, Shrimp Alkaline Phosphatase and T4 DNA Ligase from Fermentas (Vilnius, Lithuania) were used for DNA manipulation. The XYL1 gene from *Candida parapsilosis* was commercially synthesized (GenScript Corp., Piscataway, N.J., USA) with codons optimized for *S. cerevisiae* expression.

Competent *E. coli* DH5α cells were prepared and transformed as described elsewhere (Inoue et al., 1990) and transformed *E. coli* strains were selected on LB plates (Ausubel et al., 1995) containing 100 mg l$^{-1}$ ampicillin (IBI Shelton Scientific, Inc., Shelton, Conn.). *E. coli* strains were grown in LB medium containing 100 mg l$^{-1}$ ampicillin for plasmid amplifications. Yeast strains were transformed with the lithium acetate method (Güldener et al., 1996) and transformed yeast strains were selected on defined mineral medium plates containing 20 g l$^{-1}$ glucose.

Construction of TMB 3200

The *P. stipitis* XYL1 gene carrying the K270R (Lys270Arg) mutation was generated by site-directed mutagenesis using the overlap extension PCR protocol (Ho et al., 1989). In the first step, two separate PCR amplifications were made using plasmid YIplac211 PGK XYL1(K270M) (Jeppsson et al., 2006) as template, primers 5XYL1s and 3K270R (Table 5) in one reaction mix and primers 5K270R and 3XYL1s (Table 5) in the other. Primers 3K270R and 5K270R are complementary to each other. In the second step, the two PCR products were mixed with primers 5XYL1s and 3XYL1s and fused together by PCR forming XYL1(K270R). The product was cut with BamHI and inserted after the PGK1 promoter at the BglII site of YIplac211 PGK (Jeppsson et al., 2006), resulting in YIplac211 PGK XYL1(K270R). The mutation was verified by sequencing. YIplac211 PGK XYL1 (K270R) was cleaved with Bpu10I within the URA3 gene and transformed into TMB 3265 (Träff-Bjerre et al., 2004) resulting in TMB 3200.

Construction of TMB 3321, TMB 3322, TMB 3323 and TMB 3324

Primers pY7-XR-for and pY7-XR-rev (Table 5) were used to amplify ADH1p-XYL1-ADH1t with PCR. Primers pY7-XDH-for and pY7-XDH-rev (Table 5) were used to amplify PGK1p-XYL2-PGK1t. Plasmid pY7 (Walfridsson et al., 1997) was used as a template in both cases. ADH1p-XYL1-ADH1t was digested with HindIII and PstI, and PGK1p-XYL2-PGK1t was digested with PstI and SacI. The resulting fragments were inserted into YIplac128 (Gietz and Sugino, 1988) creating YIpOB1. The DNA cassette containing ADH1p-XYL1-ADH1t PGK1p-XYL2-PGK1t was excised with HindIII and SacI and inserted into YIplac211 (Gietz and Sugino, 1988) creating YIpOB2. The XYL1 gene was removed from YIpOB2 by digestion with XbaI and self-ligation to create YIpOB3. YIplac211 PGK XYL/(K270M), YIplac211 PGK XYL/(K270R) and pUC57 CpXR were digested with XbaI and the XYL1(K270M), XYL/(K270R) and XYL1(*C. parapsilosis*) fragments were inserted into the XbaI site of YIpOB3, resulting in YIpOB4, YIpOB5 and YIpOB6, respectively. Correct orientations and sequences of the inserts were verified by restriction analysis and sequencing. YIpOB2, YIpOB4, YIpOB5 and YIpOB6 were cleaved with ApaI within the URA3 gene and transformed into TMB 3044 (Karhumaa et al., 2005). This resulted in strains TMB 3321, TMB 3322, TMB 3323 and TMB 3324, respectively, henceforth referred to as Y-PsNative, Y-PsK270M, Y-PsK270R and Y-CpXR.

TABLE 4

Plasmids and *S. cerevisiae* strains used in EXAMPLE 4.

| Plasmids and Strains | Relevant genotype | Reference |
| --- | --- | --- |
| pY7 | ADH1p-XYL1-ADH1t, PGK1p-XYL2-PGK1t, URA3, 2μ | (Walfridsson et al., 1997) |
| YIplac211 PGK | PGK1p-PGK1t, URA3 | (Jeppsson et al., 2006b) |
| YIplac211 PGK XYL1(K270M) | PGK1p-XYL1(K270M)-PGK1t, URA3 | (Jeppsson et al., 2006b) |
| YIplac211 PGK XYL1(K270R) | PGK1p-XYL1(K270R)-PGK1t, URA3 | This work |
| pUC57 CpXR | XYL1(*C. parapsilosis*) | This work |
| YIplac128 | LEU2 | (Gietz and Sugino, 1988) |
| YIplac211 | URA3 | (Gietz and Sugino, 1988) |
| YIpOB1 | ADH1p-XYL1-ADH1t, PGK1p-XYL2-PGK1t, LEU2 | This work |

TABLE 4-continued

Plasmids and S. cerevisiae strains used in EXAMPLE 4.

| Plasmids and Strains | Relevant genotype | Reference |
| --- | --- | --- |
| YIpOB2 | ADH1p-XYL1-ADH1t, PGK1p-XYL2-PGK1t, URA3 | This work |
| YIpOB3 | ADH1p-ADH1t, PGK1p-XYL2-PGK1t,URA3 | This work |
| YIpOB4 | ADH1p-XYL1(K270M)-ADH1t, PGK1p-XYL2-PGK1t, URA3 | This work |
| YIpOB5 | ADH1p-XYL1(K270R)-ADH1t, PGK1p-XYL2-PGK1t, URA3 | This work |
| YIpOB6 | ADH1p-XYL1(*C. parapsilosis*)-ADH1t,PGK1p-XYL2-PGK1t, URA3 | This work |
| TMB 3265 | CEN.PK 113-11C, MATa, ura3-52, his3::HIS3 YIpXDH/XK | (Träff-Bjerre et al., 2004) |
| TMB 3200 | TMB 3265, ura3::URA3 YIplac211 PGK XYL1(K270R) | This work |
| TMB 3044 | CEN.PK 2-1C, MATa, ura3-52, Δgre3, his3::HIS3 PGK1p-XKS1-PGK1t, TAL1::PGK1p-TAL1-PGK1t, TKL1::PGK1p-TKL1-PGK1t, RKI1::PGK1p-RKI1-PGK1t, RPE1::PGK1p-RPE1-PGK1t | (Karhumaa et al., 2005) |
| TMB 3321/ Y-PsNative | TMB 3044, ura3::URA3 YIpOB2 | This work |
| TMB 3322/ Y-PsK270M | TMB 3044, ura3::URA3 YIpOB4 | This work |
| TMB 3323/ Y-PsK270R | TMB 3044, ura3::URA3 YIpOB5 | This work |
| TMB 3324/ Y-CpXR | TMB 3044, ura3::URA3 YIpOB6 | This work |

Description of Constructed Strains

Strain TMB 3200 expressing the K270R mutant of *P. stipitis* XR (Table 4) was constructed to assess the influence of the mutation on xylose fermentation by recombinant *S. cerevisiae*. The strain was compared in anaerobic continuous fermentation with TMB 3001 (Eliasson et al., 2000), which carries the native *P. stipitis* XR, XDH and overexpressed endogenous XK. Increased ethanol yield and decreased xylitol yield was observed but the xylose utilization rate was not improved (results not shown). It was suspected that the xylose utilization rate was limited by other factors than the cofactor imbalance caused by the NAD(P)H-dependent XR and the strictly $NAD^+$-dependent XDH.

Overexpression of XK together with the non-oxidative pentose phosphate pathway improved xylose utilization by recombinant *S. cerevisiae* (Karhumaa et al., 2005; Kuyper et al., 2005). Also, the deletion of the endogenous aldose reductase GRE3 minimized background XR activity and decreased xylitol formation (Träff et al., 2001). Four isogenic CEN.PK-based strains (Table 4) with these features were constructed to evaluate how the kinetic properties of XR:s affect xylose fermentation by recombinant *S. cerevisiae*. Strain Y-PsNative carrying the native *P. stipitis* XR served as a reference strain. Y-PsK270M contained the K270M mutant of *P. stipitis* XR that previously has been shown to reduce xylitol yield and increase ethanol yield in xylose fermentation (Jeppsson et al., 2006b). Y-PsK270R expressed the K270R mutant of *P. stipitis* XR and Y-CpXR contained a synthesized *C. parapsilosis* XYL1 gene (Lee et al., 2003) that had been codon optimized for *S. cerevisiae* expression.

TABLE 5

Primers used in EXAMPLE 4. Sites for restriction endonucleases are indicated in bold or italic. The codon giving the *P. stipitis* XYL1 gene Arg at amino acid position 270 is underlined in primers 5K270R and 3K270R.

| Primer | Sequence | Restriction Endonuclease |
| --- | --- | --- |
| 5XYL1s | 5'-GCGGATCC_TCTAGA_ATGCCTT-3' (SEQ. ID. NO. 10) | BamHI |
| 3XYL1s | 5'-TTGGATCC_TCTAGA_TTAGACGAAG-3' (SEQ. ID. NO. 11) | BamHI |
| 5K270R | 5'-CATCATTCCA<u>AGG</u>TCCAACACTG-3' (SEQ. ID. NO. 12) | |
| 3K270R | 5'-CAGTGTTGGA<u>CCT</u>TGGAATGATG-3' (SEQ. ID. NO. 13) | |
| pY7-XR-for | 5'-GCAAGCTT_GGCGCGCC_GGGATCGAAGAAATGATGG-3' (SEQ. ID. NO. 14) | HindIII, AscI |
| pY7-XR-rev | 5'-CGCGCGCGCTGCAGGTGTGGAAGAACGATTACAAC-3' (SEQ. ID. NO. 15) | PstI |
| pY7-XDH-for | 5'-GCCTGCAGTCTAACTGATCTATCCAAAACTG-3' (SEQ. ID. NO. 16) | PstI |
| pY7-XDH-rev | 5'-CGTGAGCTC_CGTACG_TAACGAACGCAGAATTTTC-3' (SEQ. ID. NO. 17) | SacI, BsiWI |

Example 5

Anaerobic Fermentation Using Genetically Modified Strains Carrying Mutated or Native XR Analyses Growth was followed by measuring OD620 with a Hitachi U-1800 Spectrophotometer (Hitachi Ltd., Tokyo, Japan). Concentrations of glucose, xylose, xylitol, glycerol, pyruvate, acetate, ethanol and succinate were determined by high-performance liquid chromatography (HPLC; Waters, Milford, Mass., USA) with an Aminex HPX-87 H ion exchange column (Bio-Rad, Hercules, Calif., USA), refractive index detector (RID-6A, Shimadzu, Kyoto, Japan) and UV detector (2487, Waters). The mobile phase was 5 mM $H_2SO_4$, temperature 45° C. and flow rate 0.6 ml min$^{-1}$. The composition of the outgoing gas was monitored by a Carbon Dioxide and Oxygen Monitor Type 1308 (Brüel & Kjær, Copenhagen, Denmark). Cell dry weight was determined in triplicate by filtering a known volume of culture broth through 0.45-μm Supor® 450 Membrane filters (Pall Life Sciences, Ann Arbor, Mich., USA), after which the filters were dried in a microwave oven and weighed. The fractions of protein, polysaccharides (Herbert et al., 1971), and RNA (Benthin et al., 1991) in the biomass were determined for the continuous fermentation. A previously developed stoichiometric model (Wahlbom et al., 2001) was used to estimate the intracellular carbon fluxes in continuous fermentation.

Ethanol evaporation was determined experimentally for the setup used for continuous fermentation. Ethanol was added to a fermentor sparged with a nitrogen gas flow of 0.2 l min$^{-1}$ and the ethanol concentration was measured over time. The evaporation rate followed eqn (1) with a proportionality constant of k=0.004.

$$dC_{Ethanol}/dt = -kC_{Ethanol} \quad (1)$$

Ethanol evaporation was estimated for all continuous fermentations and constitutes together with ethanol measured by HPLC the total ethanol production.

Batch Fermentation

Anaerobic batch fermentation was carried out in 3-l ADI Autoclavable Bio Reactor Systems (Applikon, Schiedam, The Netherlands) with a working volume of 1 liter. Cells were pre-cultivated in shake flasks in defined mineral medium with 20 g l$^{-1}$ glucose, washed with sterile water and inoculated into the bioreactor to an optical density at 620 nm (OD620) of 0.2. Defined mineral medium with doubled concentration of all salts, trace elements and vitamins, containing 20 g l$^{-1}$ glucose and 50 g l$^{-1}$ xylose, was used. The temperature was 30° C., stirring was set to 200 rpm and pH 5.5 was maintained by addition of 3 M KOH. Anaerobic conditions were attained by sparging with nitrogen gas containing less than 5 ppm $O_2$ (AGA GAS AB, Sundbyberg, Sweden) before inoculation. During fermentation, anaerobic conditions were maintained by the produced $CO_2$ that diffused through a water lock. The experiments were performed at least in biological duplicates.

Figure 3:
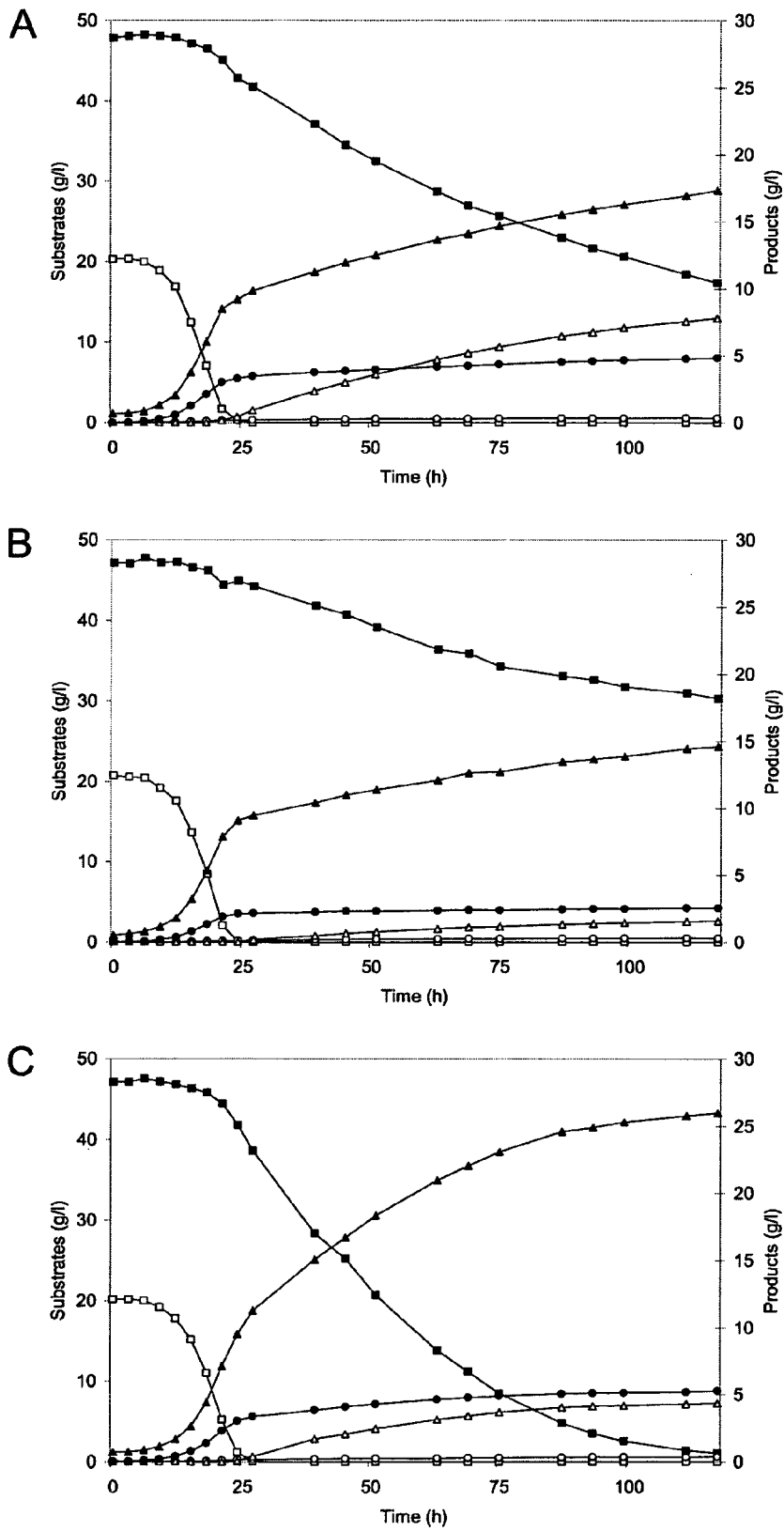
Figure 4:
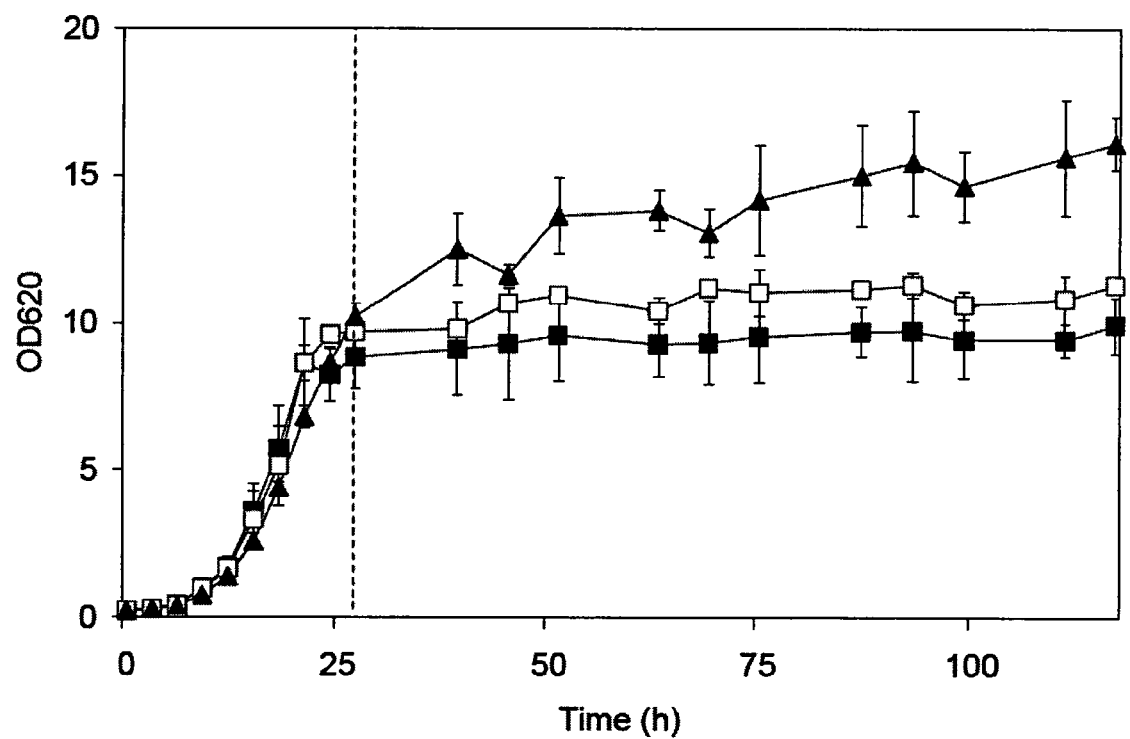
FIG. 4. Growth of strains Y-PsNative (■); Y-PsK270M (□); and Y-PsK270R (▲) in anaerobic batch culture containing 20 g $l^{-1}$ glucose and 50 g $l^{-1}$ xylose. Time of glucose depletion is indicated by the dashed line.

Strains Y-PsNative, Y-PsK270M and Y-PsK270R (cf example 4) were compared in anaerobic batch fermentation with 20 g l$^{-1}$ glucose and 50 g l$^{-1}$ xylose (FIG. 3). Table 6 summarizes xylose consumption, ethanol concentration and product yields after 117 hours of fermentation. The reference strain Y-PsNative consumed 30.4 g l$^{-1}$ xylose and produced 16.7 g l$^{-1}$ ethanol while Y-PsK270R consumed 46.1 g l$^{-1}$ xylose and produced 25.3 g l$^{-1}$ ethanol. Y-PsK270M consumed the least xylose (16.8 g l$^{-1}$) and produced the lowest ethanol concentration (14.1 g l$^{-1}$) of the three strains. The reference strain Y-PsNative produced an ethanol yield of 0.33 g ethanol g consumed sugars$^{-1}$ and a xylitol yield of 0.26 g xylitol g consumed xylose$^{-1}$. Both strains with mutated XR produced higher ethanol yields (0.38 g ethanol (g consumed sugars)$^{-1}$) and significantly lower xylitol yields (0.09 g xylitol (g consumed xylose)$^{-1}$) than the reference strain. In addition, Y-PsK270R grew and produced biomass anaerobically from xylose after glucose depletion (FIG. 4). Y-PsK270R had produced 3.4 g l$^{-1}$ biomass after 117 hours of fermentation while both Y-PsNative and Y-PsK270M produced 2.1 g l$^{-1}$ biomass.

Continuous Fermentation and Flux Analysis

Continuous fermentation was conducted anaerobically in 2-l Biostat®A bioreactors (B. Braun Biotech International, Melsungen, Germany) with a working volume of 1 liter. Defined mineral medium with 10 g l$^{-1}$ glucose and 10 g l$^{-1}$ xylose was used for pre-cultivation and continuous fermentation. Cells pre-cultivated in shake flasks and washed with sterile water were used to inoculate the bioreactor to an OD620 of 0.2. Continuous fermentation at dilution rates of 0.06 and 0.12 h$^{-1}$ was started after glucose depletion. The temperature was 30° C., stirring 200 rpm and pH 5.5 was maintained by addition of 3 M KOH. Anaerobic conditions were obtained by sparging with nitrogen gas containing less than 5 ppm $O_2$ (AGA GAS AB, Sundbyberg, Sweden) at a constant gas flow of 0.2 l min$^{-1}$ controlled by mass flow meters (Bronkhorst HI-TEC, Ruurlo, the Netherlands). The off-gas condensers were cooled to 4° C., and the medium reservoirs were continuously sparged with nitrogen gas. Steady state was assumed after five residence times, and the experiments were performed in biological duplicates.

Y-PsNative and Y-PsK270R were compared in anaerobic continuous fermentation with a feed containing 10 g l$^{-1}$ glucose and 10 g l$^{-1}$ xylose (Table 7). The continuous fermentation results were generally in agreement with the batch fermentation results. Y-PsK270R gave 4% higher ethanol yields than Y-PsNative at both dilution rates. Y-PsK270R showed 17% and 9% higher specific xylose consumption rates and gave 60% and 78% lower xylitol yields compared to the reference strain Y-PsNative at dilution rates 0.06 h$^{-1}$ and 0.12 h$^{-1}$ respectively. Y-PsK270R also gave 17% and 22% lower glycerol yields than Y-PsNative at dilution rates 0.06 h$^{-1}$ and 0.12 h$^{-1}$ respectively.

The metabolic fluxes through Y-PsNative and Y-PsK270R where estimated using a stoichiometric model (Wahlbom et al., 2001). The flux values were normalized to a total specific sugar consumption of 100 mmol g$^{-1}$ biomass h$^{-1}$. The xylose fraction of the total specific sugar consumption was smaller for both strains at dilution rate 0.12 h$^{-1}$ compared to 0.06 h$^{-1}$. According to the model, Y-PsK270R utilized a larger fraction of NADH in the XR reaction (90 and 100%) than Y-PsNative (59 and 74%) at dilution rates 0.06 h$^{-1}$ and 0.12 h$^{-1}$ respectively. The model also predicted that a smaller fraction of glucose-6-phosphate entered the oxidative pentose phosphate pathway in Y-PsK270R (11% and 7%) than in Y-PsNative (14% and 12%) at dilution rates 0.06 h$^{-1}$ and 0.12 h$^{-1}$ respectively.

TABLE 6

Xylose consumption, ethanol production and product yields after 117 hours (see FIG. 3) anaerobic batch fermentation of 20 g l$^{-1}$ glucose and 50 g l$^{-1}$ xylose by strains Y-PsNative, Y-PsK270M and Y-PsK270R.

| Strain | XR gene | Xylose consumed (g l$^{-1}$) | Ethanol produced (g l$^{-1}$) | Yields (g product (g consumed sugars)$^{-1}$) | | | | |
|---|---|---|---|---|---|---|---|---|
| | | | | Ethanol | Xylitol$^a$ | Glycerol | Biomass | Acetate |
| Y-PsNative | XYL1 | 30.4 ± 2.3 | 16.7 ± 0.4 | 0.33 ± 0.02 | 0.26 ± 0.03 | 0.095 ± 0.001 | 0.040 ± 0.001 | 0.011 ± 0.002 |
| Y-PsK270M | XYL1(K270M) | 16.8 ± 0.2 | 14.1 ± 0.3 | 0.38 ± 0.01 | 0.09 ± 0.01 | 0.067 ± 0.000 | 0.054 ± 0.001 | 0.013 ± 0.001 |
| Y-PsK270R | XYL1(K270R) | 46.1 ± 1.3 | 25.3 ± 0.5 | 0.38 ± 0.01 | 0.09 ± 0.01 | 0.079 ± 0.001 | 0.050 ± 0.001 | 0.009 ± 0.000 |

$^a$ (g xylitol (g consumed xylose)$^{-1}$)

TABLE 7

Specific consumption and production rates, product yields and carbon balances in continuous fermentation of strains Y-PsNative and Y-PsK270R under anaerobic conditions at dilution rates of 0.06 h$^{-1}$ and 0.12 h$^{-1}$ with 10 g l$^{-1}$ glucose and 10 g l$^{-1}$ xylose.

| Dilution rate (h$^{-1}$) | Strain | Specific consumption and production rates (g (g biomass)$^{-1}$ h$^{-1}$) | | | Yields (g product (g consumed sugars)$^{-1}$) | | | | | Carbon balance (%) |
|---|---|---|---|---|---|---|---|---|---|---|
| | | Glucose | Xylose | Ethanol | Ethanol | Xylitol$^a$ | Glycerol | CO$_2$ | Biomass | |
| 0.06 | Y-PsNative | −0.64 ± 0.02 | −0.19 ± 0.01 | 0.31 ± 0.00 | 0.37 ± 0.02 | 0.30 ± 0.02 | 0.090 ± 0.004 | 0.30 ± 0.00 | 0.073 ± 0.003 | 96 ± 2 |
| | Y-PsK270R | −0.52 ± 0.01 | −0.22 ± 0.01 | 0.29 ± 0.01 | 0.39 ± 0.00 | 0.12 ± 0.01 | 0.074 ± 0.009 | 0.30 ± 0.01 | 0.081 ± 0.002 | 94 ± 1 |
| 0.12 | Y-PsNative | −1.09 ± 0.03 | −0.26 ± 0.02 | 0.50 ± 0.01 | 0.37 ± 0.02 | 0.24 ± 0.04 | 0.092 ± 0.005 | 0.30 ± 0.01 | 0.089 ± 0.003 | 95 ± 3 |
| | Y-PsK270R | −1.04 ± 0.06 | −0.28 ± 0.01 | 0.51 ± 0.03 | 0.39 ± 0.01 | 0.05 ± 0.02 | 0.072 ± 0.011 | 0.30 ± 0.00 | 0.091 ± 0.004 | 93 ± 1 |

$^a$(g xylitol (g consumed xylose)$^-$

Example 6

Kinetic Analysis of Mutated and Native *Piccia stipitis* XR

Enzymatic Activity and Kinetic Properties of Native and Mutated XR

Strains were cultivated for enzyme activity measurements in defined mineral medium containing 20 g l$^{-1}$ glucose and harvested in the exponential growth phase. Cells were washed with sterile water and treated with yeast protein extraction solution Y-PER (Pierce, Rockford, Ill., USA). Coomassie Protein Assay Reagent (Pierce) was used to determine protein concentration with Albumin Standard (Pierce). NAD(P)H-dependent XR activity was determined using an Ultrospec 2100 pro spectrophotometer (Amersham Biosciences, Uppsala, Sweden) operating at 30° C. and 340 nm ($\epsilon_{NAD(P)H}$=6220 M$^{-1}$ cm$^{-1}$). Triethanolamine buffer (100 mM, pH 7.0) was used and reactions were started by the addition of xylose. Functional XR expression was confirmed using a standard assay with 200 μM NAD(P)H and 350 mM xylose as previously described (Eliasson et al., 2000). XR kinetics in crude extracts from strains Y-PsNative, Y-PsK270M and Y-PsK270R (cf example 4) were determined, with concentrations of xylose and NAD(P)H varied over at least five levels, ranging from less than half to more than 5 times the respective apparent K$_m$ value. The initial rates were fitted by unconstrained nonlinear optimization in MatLab R2006a to eqn (2), which describes the initial rate for a two substrate reaction following a compulsory-order ternary-complex mechanism (Cornish-Bowden, 2004).

$$v = V_{max}[A][B]/(K_{iA}K_{mB} + K_{mB}[A] + K_{mA}[B] + [A][B]) \quad (2)$$

$V_{max}$ is the maximum velocity, [A] and [B] are the concentrations of NAD(P)H and xylose, respectively, $K_{mA}$ and $K_{mB}$ are the Michaelis constants of NAD(P)H and xylose, respectively, and $K_{iA}$ is the dissociation constant of NAD(P)H.

Crude extracts of strains Y-PsNative, Y-PsK270M, Y-PsK270R and Y-CpXR were analyzed for functional XR expression with a standard assay (200 μM NAD(P)H, 350 mM xylose) (Table 8). Y-PsK270M displayed only about 34% and 36% of the NADPH and NADH dependent XR activities compared to the reference strain Y-PsNative. In contrast, Y-PsK270R showed 2.4-fold and 3.2-fold higher NADPH and NADH dependent XR activities compared to Y-PsNative. Y-CpXR with the *C. parapsilosis* XYL1 did not display any significant NADPH or NADH dependent XR activity. The two *P. stipitis* XR mutants displayed no change of cofactor preference compared to the native XR under standard assay conditions (Table 8).

A kinetic study was made on crude extracts from strains Y-PsNative, Y-PsK270M and Y-PsK270R. The data was fitted to eqn (2) and the resulting constants are summarized in Table 8. Compared with native XR from *P. stipitis*, the K270M mutation resulted in a significant increase in the K$_m$ values for both NADPH and NADH. In fact, the kinetic parameters for the NADH-linked reaction catalyzed by the K270M mutant could not even be determined since this mutant could not be saturated with NADH. The K270R mutation increased the K$_m$ value for NADPH 25-fold, while the K$_m$ for NADH only increased 2-fold.

TABLE 8

Specific XR activity in cell extracts from strains Y-PsNative, Y-PsK270M, Y-PsK270R and Y-CpXR in standard conditions (200 μM NAD(P)H, 350 mM xylose) and estimated kinetic parameters for NAD(P)H reduction of xylose by corresponding cell extracts.

| Strain | XR gene | Cofactor | Specific XR activity U mg$^{-1}$ protein | $K_{mA}$ μM | $K_{mB}$ mM | $K_{iA}$ μM | $V_{max}$ U mg$^{-1}$ protein |
|---|---|---|---|---|---|---|---|
| Y-PsNative | XYL1 | NADPH | 0.23 ± 0.06 | 1.0 ± 0.6 | 62.2 ± 27.7 | 1.4 ± 1.2 | 0.30 ± 0.05 |
|  |  | NADH | 0.10 ± 0.02 | 28.7 ± 5.4 | 59.2 ± 10.5 | 25.9 ± 11.7 | 0.21 ± 0.01 |
| Y-PsK270M | XYL1(K270M) | NADPH | 0.08 ± 0.01 | 290 ± 78.6 | 454 ± 142 | 293 ± 169 | 0.91 ± 0.09 |
|  |  | NADH | 0.04 ± 0.01 | — | — | — | — |
| Y-PsK270R | XYL1(K270R) | NADPH | 0.54 ± 0.02 | 25.8 ± 9.1 | 468 ± 151 | 22.9 ± 17.6 | 2.13 ± 0.24 |
|  |  | NADH | 0.32 ± 0.02 | 62.8 ± 18.7 | 145 ± 36.9 | 57.4 ± 34.9 | 0.96 ± 0.09 |
| Y-CpXR | XYL1(C. parapsilosis) | NADPH | n.d. | — | — | — | — |
|  |  | NADH | n.d. | — | — | — | — |

$K_{mA}$ and $K_{mB}$ are the Michaelis constants of NAD(P)H and xylose, respectively, $K_{iA}$ is the dissociation constant of NAD(P)H and $V_{max}$ is the maximum velocity.
n.d. not detected, — not determined

Example 7

Strain Construction

The XYL1(K270R) gene fragment was excised from plasmid YIpOB5 (Table 9) and inserted into YIpOB7 (Table 9), carrying P. stipitis XDH gene, using the XbaI restriction sites, creating plasmid YIpOB9 (Table 9), an integrative plasmid harboring XYL1(K270R) gene under the control of TDH3 promoter and P. stipitis XYL2 gene under the control of PGKJ promoter. Strain TMB3043 (Karhumaa et al., 2005) was transformed with the integrative plasmid YIPOB9, and the new strain was named TMB3662. Strain TMB3662 was transformed with the integrative plasmid YIplac128 (Gietz and Sugino, 1988), and the new strain was named TMB3415.

TABLE 9

Plasmids and strains used in EXAMPLE 7

| Plasmid | Features | Reference |
|---|---|---|
| YIpOB5 | ADH1p-XYL1(K270R)-ADH1t, PGK1p-XYL2-PGK1t, URA3 | This work |
| YIpOB7 | TDH3p-ADH1t, PGK1p-XYL2-PGK1t, URA3 | This work |
| YIpOB9 | TDH3p-XYL1(K270R)-ADH1t, PGK1p-XYL2-PGK1t, URA3 | This work |
| YIplac128 | Integrative plasmid, LEU2 | (Gietz and Sugino, 1988) |

| Strain | Genotype | Reference |
|---|---|---|
| TMB3043 | CEN.PK 2-1C, MATa, leu2-3 112, ura3-52, Δgre3, his3::HIS3 PGK1p-XKS1-PGK1t, TAL1::PGK1p-TAL1-PGK1t, TKL1::PGK1p-TKL1-PGK1t, RKI1::PGK1p-RKI1-PGK1t, RPE1::PGK1p-RPE1-PGK1t | (Karhumaa, et al., 2005) |
| TMB3662 | TMB3043, YIpOB9 | This work |
| TMB3415 | TMB3662, YIplac128 | This work |

Two-Phase Aerobic/Anaerobic Fermentation

Strain TMB3415 was used for two-phase aerobic/anaerobic fermentation experiments.

Aerobic growth Erlenmeyer baffled flasks and two-phase aerobic/anaerobic fermentation were performed in mineral medium (Jeppsson et al., 2006). The medium contained 60 g l$^{-1}$ xylose (Acros Organics, Geel, Belgium) as sole carbon source. When used for fermentation in bioreactor, the medium was supplemented with 0.4 g l$^{-1}$ Tween 80 (Sigma-Aldrich, St. Louis, USA), 0.01 g l$^{-1}$ ergosterol (Alfa Aesar, Karlsruhe, Germany).

S. cerevisiae was grown aerobically in Erlenmeyer baffled flasks filled to maximum ¹/₁₀ of the volume with medium, incubated at 30° C. in a rotary shake-incubator (INR-200 shake incubator, Gallenkamp, Leicester, UK) at 200 rpm.

Two-phase aerobic/anaerobic batch fermentation was performed in 2 l working volume bioreactors (Applikon Biotechnology, Schiedam, The Netherlands), for at least 175 h in total, at 30° C., at pH 5.5 automatically controlled by addition of 3M KOH. Prior to inoculation, aerobic conditions were established by sparging sterile air at 0.4 l min$^{-1}$ flow rate with constant stirring at 500 rpm.

Figure 5:
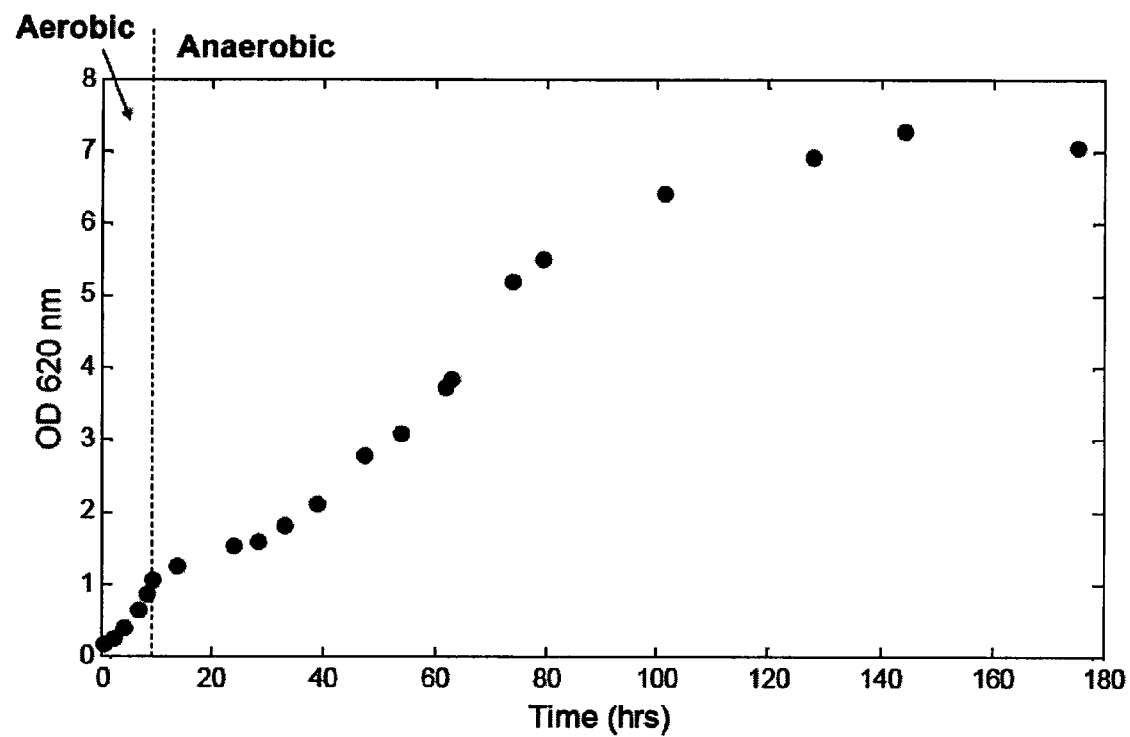
FIG. 5. Representative plot of biomass production during two-phase aerobic/anaerobic fermentation of strain TMB3415

Cells were pre-grown aerobically in shake flasks in defined mineral medium (Jeppsson at al., 2006), harvested by centrifugation, resuspended in ~10 ml sterile medium and inoculated in the fermentor at an initial O.D.$_{620nm}$ of 0.2±0.02. Aerobic growth on xylose was followed by OD measurement. At O.D.$_{620nm}$=1.0 air feed was switched to $N_2$ (<5 ppm $O_2$, AGA, Malmö, Sweden) at 0.2 l min$^{-1}$ flow rate in order to establish anaerobic conditions. Oxygen free conditions were ensured by measuring the off-gas composition and the dissolved oxygen concentration in the fermentor. Anaerobic growth and ethanol production were followed for at least 165 hours. Experiments were performed at least in duplicate. A representative plot of biomass production during aerobic and anaerobic conditions is depicted in FIG. 5.

At each sampling point, samples were drawn from the fermentors after discharging the sample tubing dead-volume, cells were quickly separated by centrifugation and the supernatant was stored at −20° C. until further analysis.

Concentrations of xylose, xylitol acetate, glycerol and ethanol were determined by high performance liquid chromatography (HPLC) (Waters, Milford, Mass., US). The compounds were separated with an Aminex HPX-87H resin-based columns (Bio-Rad, Hercules, Calif., US) preceded a Micro-Guard Cation-H guard column (Bio-Rad, Hercules, Calif., US). Separation was performed at 45° C., with 5 mM sulphuric acid at a flow rate of 0.6 ml min$^{-1}$ as mobile phase. Compounds were detected by UV or refractive index detection (Shimadzu, Kyoto, Japan). Each sample was analyzed at least in duplicate.

Oxygen and $CO_2$ concentration in the outlet exhaust of the fermentor was constantly monitored with a Carbon Dioxide and Oxygen Monitor Type 1308 (Brüel and Kjaer, Copenhagen, Denmark).

For each fermentation experiment, dry weight measurements were made in two points at least, in triplicate for each point. The end point of the aerobic phase (O.D.$_{620nm}$=1.0) and the point O.D.$_{620nm}$=4.0 in the anaerobic phase at were always included. For dry weight determination, a known volume of cell culture was filtered through dry pre-weighed 0.45 µm nitrocellulose filters, which were subsequently dried in a microwave oven and weighed.

The maximum specific growth rate, µ, was calculated for both the aerobic and the anaerobic phase from exponential fitting of $O.D._{620nm}$ vs. time. Xylose uptake and products formation rates were calculated for the anaerobic phase by assuming a pseudo-steady state during exponential anaerobic growth, between $O.D._{620nm}=1.0$ and $O.D._{620nm}=6.0$. Pseudo-steady state was validated by observing constant consumption and production rates within the measurement range. Rates of product formation and substrate consumption were calculated by nonlinear regression on measured values of analyte and biomass concentration. Carbon balance of the calculated rates closed to 95-105%.

The calculated maximum specific growth rate for the aerobic phase was $0.2\ h^{-1}$, while the calculated maximum specific growth rate for the anaerobic phase was $0.0237\ h^{-1}$. Calculated rates are reported in Table 10, where: $r_x$, specific biomass production rate; $r_s$, specific substrate consumption rate; $r_e$, specific ethanol production rate; $r_g$, specific glycerol production rate; $r_a$, specific acetate production rate; $r_{xol}$, specific xylitol production rate; $r_{co2}$, specific $CO_2$ production rate; Ysx, biomass produced per unit of consumed substrate; $Y_{se}$, ethanol produced per unit of consumed substrate; $Y_{sxol}$, xylitol produced per unit of consumed substrate.

TABLE 10

Rates and yields during anaerobic xylose growth of TMB 3415.

| Uptake/Production rate (g × (gDW × h)$^{-1}$) | | | | | | | Yield factors (g/g) | | |
|---|---|---|---|---|---|---|---|---|---|
| $r_x$ | $r_s$ | $r_e$ | $r_g$ | $r_a$ | $r_{xol}$ | $r_{co2}$ | $Y_{sx}$ | $Y_{se}$ | $Y_{sxol}$ |
| 0.0237 | −0.321 | 0.121 | 0.0104 | 0 | 0.0584 | 0.120 | 0.0738 | 0.38 | 0.18 |

References

Gietz, R. D. and Sugino, A. (1988). New yeast-*Escherichia coli* shuttle vectors constructed with in vitro mutagenized yeast genes lacking six-base pair restriction sites. Gene 74, 527-534.

Jeppsson, M., Bengtsson, O., Franke, K., Lee, H., Hahn-Hägerdal, B. and Gorwa-Grauslund, M. F. (2006). The expression of a *Pichia stipitis* xylose reductase mutant with higher K(M) for NADPH increases ethanol production from xylose in recombinant *Saccharomyces cerevisiae*. Biotechnol Bioeng 93, 665-673.

Karhumaa et al. (2005). Investigation of limiting metabolic steps in the utilization of xylose by recombinant *Saccharomyces cerevisiae* using metabolic engineering. Yeast. 22(5):359-368.

van Dijken, J. P., Bauer, J., Brambilla, L., Duboc, P., Francois, J. M., Gancedo, C., Giuseppin, M. L. F., Heijnen, J. J., Hoare, M., Lange, H. C., Madden, E. A., Niederberger, P., Nielsen, J., Parrou, J. L., Petit, T., Porro, D., Reuss, M., van Riel, N., Rizzi, M., Steensma, H. Y., Verrips, C. T., Vindeløv, J. and Pronk, J. T. (2000). An interlaboratory comparison of physiological and genetic properties of four *Saccharomyces cerevisiae* strains. Enz Microb Technol 26, 706-714.

Example 8

Construction of Strains Overexpressing the PGM2 Gene

Expression of PGM2 on a Multicopy Plasmid

The multicopy plasmid YEplacHXT (Karhumaa, Hahn-Hagerdal et al. 2005) was used to introduce multiple copies of PGM2 gene in strain CENPK 113-11C (Entian and Kötter 1998). The YEplacHXT vector (Karhumaa, Hahn-Hägerdal et al. 2005) was double digested with BamHI and PstI to linearize it between the HXT7' promoter (Hauf, Zimmermann et al. 2000) and PGK terminator. Transformation of *S. cerevisiae* CEN-PK 113-11C with the cleaved vector YEplacHXT generated strain TMB 3126 (Table 11). The PGM2 gene was amplified from genomic DNA of TMB 3400 (Table 11) (Wahlbom, van Zyl et al. 2003) with primers that had overhangs (underlined) homologous to the end of HXT7' promoter (5'TTTTTTAATTTTAATCAAAAAAGGAT CCCCGGGCTGCAATGTCATTTC AATTGAAACG-3' (SEQ ID. NO. 18)') and the beginning of PGK terminator (5'CCACCACCAGTAGAGACATGGGAGATCTAGAA TTCCTTTAAGTACGAA CCGTTGG-3' (SEQ. ID. NO. 19)) to enable double recombination between PGM2 with overhangs and the linearized plasmid to form the plasmid YEplacHXT-PGM2 (Table 11) while yeast was transformed generating strain TMB 3127 (Table 11). Transformant colonies were selected on defined medium supplemented with histidine and uracil was excluded to select for recovery of auxotrophy. The YDp-H plasmid was extracted from *E. coli* JM101 to be used as template for amplification of the HIS3 locus by PCR with the primers his3YDpH_prom 5'GCGATTGGCATTATCAC 3' (SEQ. ID. NO. 20) and his3YDpH-rev 5'GCAGCTTTAAATAATCGG 3' (SEQ. ID. NO. 21). The HIS3 amplicon was transformed and integrated in yeast strains TMB 3126 and TMB 3127, to generate strains Control m, TMB 3128, and PGM2 m, TMB 3129, respectively (Table 11). Transformants were selected on defined mineral medium without supplementation. Plasmids were rescued and transformed into *E. coli* DH5α for verification. Analytical PCR of recovered plasmids confirmed that the extra copy of PGM2 under the HXT7p' was present in PGM2 m but not in the Control m strain.

Genomic Integration of PGM2

For the construction of the strains Control i, TMB 3135 and PGM2 i, TMB 3136 (Table 11), the HIS3 amplicon was transformed into *S. cerevisiae* CEN-PK 113-11C as described above to generate strain TMB 3134 (Table 11). Yeast transformants were selected on defined mineral medium supplemented with uracil. The purified plasmid YEplacHXT-PGM2 (Table 11) from strain PGM2 m was used as template to PCR amplify with PWO-polymerase the amplicon HXT7 p-PGM2-PGKt with overhangs to include Sal I restriction sites to be cloned into the integrative vector YIplac211 (Gietz and Sugino 1988) (Table 11), using primers: PGK SalI (5' ATCTGTCGACGACATAGAAATATCGAATGG 3' (SEQ.

ID. NO. 22)) homologous to PGKt and HXT SalI (5' ATCT-GTCGACAGGAACAATTTCGGGCC 3' SEQ. ID. NO. 23)) homologous to HXT7' p (homologous sequences are underlined). The PCR product HXT7' p-PGM2-PGKt and the vector YIplac211 were cleaved with restriction enzyme SalI and treated with SAP enzyme. PCR product HXT7' p-PGM2-PGKt and the cleaved vector YIplac211 were ligated with T4 ligase enzyme. The ligation mixture was transformed into E. coli DH5α competent cells and transformants were selected on LB plates with 100 mg/L ampicillin. To verify positive transformants carrying YIplac211 HXT-PGM2, several clones were selected and grown overnight on LB liquid medium with 100 mg/L ampicillin. Plasmids were extracted and cleaved with restriction enzymes to confirm the proper size of the cleaved fragments and also by analytical PCR.

Purified plasmids YIplac211 and YIplac211 HXT-PGM2 (Table 11) from E. coli were cleaved in the URA locus EcoRV and treated with SAP. Plasmids were used to transform the yeast strain TMB 3134 targeting the URA locus. Thus strain Control i, TMB 3135, was generated by integration of cleaved YIplac211 and strain PGM2 i, TMB 3136, by integration of YIplac211 HXT-PGM2 (Table 11). Transformants were selected on defined mineral medium without supplementation.

Genomic integration of HXT7' p-PGM2-PGKt was verified by analytical PCR of genomic DNA extracted from Control i and PGM2 i.

PGM2 Overexpression in Xylose Utilizing Strains

The xylose utilizing strain TMB 3320 (Bengtsson, Bettiga et al. Submitted)(Table 11), which has been genetically modified to improve xylose fermentation (Träff, Otero Cordero et al. 2001; Jeppsson, Johansson et al. 2002; Karhumaa, Hahn-Hägerdal et al. 2005) was transformed with EcoRV linearized plasmids YIplac211 and YIplac211 HXT-PGM2 in the URA locus (Table 11), to generate strains Control-PPP-XYL, TMB 3137, and strain PGM2-PPP-XYL, TMB 3138, respectively (Table 11).

Other xylose utilizing strains were constructed from strain CEN PK 113-11C hence harboring less genetic modifications known to favour xylose utilization. Plasmid YIpXR/XDH/XK (Eliasson, Christensson et al. 2000) (Table 11) was extracted from E. coli DH5α and cleaved with PstI in the HISS locus. The linearized plasmid was transformed into S. cerevisiae strain CENPK 113-11C. Transformants were selected on defined mineral medium supplemented with uracil. Integration of genes encoding the xylose pathway was verified by growth on defined medium with 50 g/l xylose. Strain CENPK 113-11C harbouring the integrated YIpXR/XDH/XK was further transformed with plasmids YIplac211 and YIplac211HXT-PGM2 (Table 11) that were cleaved in the URA-locus with EcoRV. The strain harbouring integrated YIplac211 and YIpXR/XDH/XK was named Control-XYL, TMB 3139, and the one harbouring YIplac211 HXT-PGM2 and YIpXR/XDH/XK was named PGM2-XYL, TMB 3140 (Table 11). Transformants were selected on defined mineral medium without nutrient supplementation. Positive transformants recovered uracil auxotrophy.

Genomic DNA was extracted from Control-PPP-XYL, PGM2-PPP-XYL, Control-XYL and PGM2-XYL and by analytical PCR integration events were verified.

TABLE 11

Plasmids and S. cerevisiae strains used in EXAMPLE 8

| Plasmids/Strains(*) | Relevant genotype/phenotype | Reference |
|---|---|---|
| Plasmids | | |
| YEplacHXT | YEplac195, HXT7p-PGKt URA3 | (Karhumaa, Hahn-Hägerdal et al. 2005) |
| YEplacHXT-PGM2 | YEplac195, HXT7p-PGM2-PGKt URA3 | (Garcia Sanchez R., Hahn-Hägerdal B. et al. Manuscript in preparation 2009) |
| YDp-H | used to amplify HIS3 to recover the auxotrophy | (Berben, Dumont et al. 1991) |
| YIplac211 | URA3 | (Gietz and Sugino 1988) |
| YIplac211 HXT-PGM2 | YIpac211, HXT7p-PGM2-PGKt URA3 | (Garcia Sanchez R., Hahn-Hägerdal B. et al. Manuscript in preparation 2009) |
| YIpXR/XDH/XK | ADHp XYL1 ADHt, PGKp XYL2 PGKt, PGKp XK PGKt, HIS3, β-lactamase | (Eliasson, Christensson et al. 2000) |
| S. cerevisiae strains | | |
| TMB 3400 | genomic DNA used as template to amplify PGM2 | (Wahlbom, van Zyl et al. 2003) |
| CEN.PK 113-11C | MATa his3Δ1 ura 3-52 MAL2-8c SUC2 | (Entian and Kötter 1998) |
| TMB 3126 | CEN PK 113-11C, his3Δ1 YEplacHXT URA3 | (Garcia Sanchez R., Hahn-Hägerdal B. et al. Manuscript in preparation 2009) |
| TMB 3127 | CEN PK 113-11C, his3Δ1 YEplacHXT-PGM2 URA3 | (Garcia Sanchez R., Hahn-Hägerdal B. et al. Manuscript in preparation 2009) |
| TMB 3128 "Control m" | TMB 3126 his3::HIS3 YEplacHXT URA3 | (Garcia Sanchez R., Hahn-Hägerdal B. et al. Manuscript in preparation 2009) |
| TMB 3129 "PGM2 m" | TMB 3127 his3::HIS3 YEplacHXT-PGM2 URA3 | (Garcia Sanchez R., Hahn-Hägerdal B. et al. Manuscript in preparation 2009) |

TABLE 11-continued

Plasmids and *S. cerevisiae* strains used in EXAMPLE 8

| Plasmids/Strains(*) | Relevant genotype/phenotype | Reference |
|---|---|---|
| TMB 3134 | CENPK 113-11C, his3::HIS3 | (Garcia Sanchez R., Hahn-Hägerdal B. et al. Manuscript in preparation 2009) |
| TMB 3135 "Control i" | CENPK 113-11C, his3::HIS3 ura3::URA3 | (Garcia Sanchez R., Hahn-Hägerdal B. et al. Manuscript in preparation 2009) |
| TMB 3136 "PGM2 i" | CENPK 113-11C, his3::HIS3 ura3::URA3 HXT7'p-PGM2-PGKt | (Garcia Sanchez R., Hahn-Hägerdal B. et al. Manuscript in preparation 2009) |
| TMB 3320 | CEN.PK2-1C, Δgre3 his3::HIS3 PGK1p-XK1-PGK1t, PGK1p-TAL1-PGK1t, PGK1p-RKI1-PGK1t, PGK1p-TKL1-PGK1t, PGK1p-RPE1-PGK1t, TRP1, leu2::LEU2 ADH1p-XR-ADH1t PGKp-XDH-PGKt ura3 | (Bengtsson, Bettiga et al. Submitted) |
| TMB 3139 "Control-XYL" | CENPK 113-11C, YIpXR/XDH/XK URA3 HIS3 | (Garcia Sanchez R., Hahn-Hägerdal B. et al. Manuscript in preparation 2009) |
| TMB 3140 "PGM2-XYL" | CENPK 113-11C, YIpXR/XDH/XK, YIplac HXT-PGM2 | (Garcia Sanchez R., Hahn-Hägerdal B. et al. Manuscript in preparation 2009) |
| TMB 3137 "Control-PPP-XYL" | TMB 3320, ura3::URA3 YIplac211 | (Garcia Sanchez R., Hahn-Hägerdal B. et al. Manuscript in preparation 2009) |
| TMB 3138 "PGM2-PPP-XYL" | TMB 3320, ura3::URA3 YIplac HXT-PGM2 | (Garcia Sanchez R., Hahn-Hägerdal B. et al. Manuscript in preparation 2009) |

(*)Abbreviations of the most important genetic features are shown in quotation marks Bengtsson, O., M. Bettiga, et al. (Submitted). "Differential behaviour of two commonly used promoters in xylose utilizing recombinant *Saccharomyces cerevisiae*."

Berben, G., J. Dumont, et al. (1991). "The YDp plasmids: a uniform set of vectors bearing versatile gene disruption cassettes for *Saccharomyces cerevisiae*." *Yeast* 7(5): 475-7.

Eliasson, A., C. Christensson, et al. (2000). "Anaerobic xylose fermentation by recombinant *Saccharomyces cerevisiae* carrying XYL1, XYL2, and XKS1 in mineral medium chemostat cultures." *Appl Environ Microbiol* 66(8): 3381-6.

Entian, K. and P. Kötter (1998). "Yeast mutant and plasmid collections." *Yeast gene analysis* Edited by Brown J P A, and Tuite M F. San Diego. Calif. Academic Press 26: 431-449.

Garcia Sanchez R., Hahn-Hägerdal B., et al. (Manuscript in preparation 2009). "PGM2 overexpression improves fermentation of galactose and/or xylose."

Gietz, R. D. and A. Sugino (1988). "New yeast-*Escherichia coli* shuttle vectors constructed with in vitro mutagenized yeast genes lacking six-base pair restriction sites." *Gene* 74(2): 527-34.

Hauf, J., F. K. Zimmermann, et al. (2000). "Simultaneous genomic overexpression of seven glycolytic enzymes in the yeast *Saccharomyces cerevisiae*." *Enzyme Microb Technol* 26(9-10): 688-698.

Jeppsson, M., B. Johansson, et al. (2002). "Reduced oxidative pentose phosphate pathway flux in recombinant xylose-utilizing *Saccharomyces cerevisiae* strains improves the ethanol yield from xylose." *Appl Environ Microbiol* 68(4): 1604-9.

Karhumaa, K., B. Hahn-Hägerdal, et al. (2005). "Investigation of limiting metabolic steps in the utilization of xylose by recombinant *Saccharomyces cerevisiae* using metabolic engineering." *Yeast* 22(5): 359-68.

Träff; K. L., R. R. Otero Cordero, et al. (2001). "Deletion of the GRE3 aldose reductase gene and its influence on xylose metabolism in recombinant strains of *Saccharomyces cerevisiae* expressing the xylA and XKS1 genes." *Appl Environ Microbiol* 67(12): 5668-74.

Wahlbom, C. F., W. H. van Zyl, et al. (2003). "Generation of the improved recombinant xylose-utilizing *Saccharomyces cerevisiae* TMB 3400 by random mutagenesis and physiological comparison with *Pichia stipitis* CBS 6054." *FEMS Yeast Res* 3(3): 319-26.

Example 9

Aerobic Cultivation with Strains Expressing PGM2

Yeast Nitrogen Base medium (YNB) (6.7 g/l Difco Yeast Nitrogen Base without aminoacids; Becton, Dickinson and Company, Sparks, Md., USA) was supplemented with 50 g/l xylose as sole carbon source to assess growth. YNB liquid medium was buffered with potassium hydrogen phthalate (10.21 g/l phthalate, 2.1 g/l KOH, pH 5.5)(Hahn-Hagerdal, Karhumaa et al. 2005). The concentration of YNB was doubled when the sugar concentration was more than 20 g/l to avoid nutrient limitation. Pre-cultures and aerobic batch cultivation experiments were performed at 30° C. and 180-200 rpm agitation (Gallenkamp INR-200, Leicester, UK). Pre-cultures grown in YNB with 20 g/l glucose until mid-late exponential phase overnight on 50 ml tubes with approximately 5 ml growth medium were used to inoculate aerobic batch cultures at $OD_{620\,nm}$ 0.1-0.2 in cotton-stoppered baffled 500 ml flasks with 50 ml growth medium. Aerobic growth cultures were performed at least in duplicate.

Defined mineral medium (YNB) was supplemented with aminoacids or cyclic nitrogenous bases for auxotrophic strains when required for selection. Histidine and uracil were added at a concentration of 40 mg/L and 20 mg/L, respectively (Hahn-Hagerdal, Karhumaa et al. 2005).

Plates were supplemented with 20 g/l glucose and 20 g agar/l. The $_\mu$max were determined on xylose medium for the xylose consuming strains (Table 12). Strains overexpressing the non-oxidative PPP and with Δgre3, i.e strains Control-PPP-XYL and PGM2-PPP-XYL, had three to four fold higher growth rate on xylose than the strains Control-XYL and PGM2-XYL (Table 12), confirming that the additional genetic modifications enhance xylose consumption (Traff, Otero Cordero et al. 2001; Johansson and Hahn-Hagerdal 2002; Karhumaa, Hahn-Hagerdal et al. 2005). Strain PGM2-PPP-XYL had increased the $\mu_{max}$ aerobically on xylose medium compared to that of Control-PPP-XYL strain.

TABLE 12

Maximum specific growth rate $\mu_{max}$ ($h^{-1}$) ± standard deviation in aerobic defined medium with 50 g/l xylose

| Strain | $\mu_{max}$ ($h^{-1}$) |
|---|---|
| Control-PPP-XYL | 0.038 ± 0.014 |
| PGM2-PPP-XYL | 0.041 ± 0.008 |
| Control-XYL | 0.012 ± 0.002 |
| PGM2-XYL | 0.012 ± 0.003 |

Anaerobic Fermentation on Xylose with Strains Expressing PGM2

Anaerobic fermentation was performed in defined mineral medium (Jeppsson, Bengtsson et al. 2006). The medium was supplemented with 0.4 g/l Tween 80 and 0.01 g/l ergosterol, and 20 g/l xylose.

The pre-culture medium contained 20 g/l glucose and was buffered with phthalate buffer (10.21 g/l phthalate, 2.1 g/l KOH, pH 5.5) (Hahn-Hagerdal, Karhumaa et al. 2005). A first pre-culture was inoculated and grown until late exponential phase in 5 ml culture in 50 ml tubes. The culture was used to inoculate a second aerobic pre-culture of 100 ml in 1000 ml cotton-stoppered baffled shake flasks. Cells from the second pre-culture were grown until late exponential phase and used to inoculate anaerobic batch cultures at $OD_{620\,nm}$ of 0.1-0.2. Cells were washed twice with sterile water and centrifuged at 5000 rpm for 10 min. Aerobic pre-cultures were grown at 30° C. (Gallenkamp INR-200, Leicester, UK) and 180-200 rpm.

Anaerobic batch fermentation was performed in either 3 L Biostat® Bio Reactors (B. Braun Biotech International, Melsungen, Germany) or 3 L Applikon® Bio Reactors (Applikon, Schiedam, The Netherlands) with a working volume of 1.5 L, at 30° C. and 200 rpm, pH was controlled at 5.5 with 3M KOH. Anaerobic conditions were obtained by flushing nitrogen gas containing less than 5 ppm $O_2$ (AGA Gas, Sundbyberg, Sweden) from the bottom of the bio reactor at a flow rate of 0.2 l/min controlled by a gas mass flow-meter (Bronkhorst, HI-TECH, Ruurlo, The Netherlands). Outlet carbon dioxide and oxygen concentrations were monitored by a Carbon Dioxide and Oxygen Monitor type 1308 (Brüel & Kjaer, Copenhagen, Denmark).

Anaerobic fermentation experiments were performed at least in duplicate with less than 10% difference.

Results from the anaerobic batch cultivation on 20 g/l xylose with the strains Control-PPP-XYL and PGM2-PPP-XYL are shown in FIG. 6A for sugar consumption and product formation and in FIG. 6B for anaerobic growth. The specific growth rate was 0.03±0.01 ($h^{-1}$) for strain Control-PPP-XYL and 0.07±0.01 for strain PGM2-PPP-XYL. The strain overexpressing an extra copy of PGM2 increased the flux through the xylose utilization pathway. In the strain PGM2-PPP-XYL metabolite distribution changed by an increase in biomass and ethanol yield and a decrease in glycerol and xylitol yield.

Example 10

Enzymatic Activity for Phosphoglucomutase

PGM activity was determined in crude extracts of cells grown on YNB medium containing 20 g/l galactose or 20 g/l glucose. For every strain and condition, at least 3 independent cultures were grown and at least 2 independent enzymatic measurements were performed with different dilutions of the same cell extract. Cells were harvested in exponential phase, centrifuged at 5000 rpm for 5 min, washed with sterile water and permeabilized with Y-PER (Pierce, Rockford, Ill., USA). The protein concentration was determined with Coomassie Protein Assay Reagent (Pierce, Rockford, Ill., USA), using bovine serum albumin as standard. Phosphoglucomutase activity was determined at 30° C. by monitoring NAPDH production at 340 nm as previously described (Bro, Knudsen et al. 2005). The chemicals used to determine enzyme activity were purchased from Sigma-Aldrich (St. Louis, Mo., USA).

Two strains with different numbers of copies of the gene PGM2 were constructed with the same genetic background (cf example 9; Table 11). In both strains, PGM2 was expressed under the control of the constitutive promoter HXT7' (Hauf, Zimmermann et al. 2000). One strain overexpressed PGM2 from a multicopy plasmid and was named PGM2 m. Its control strain Control m carried the same plasmid without the structural gene. Another strain expressed only one additional integrated copy of PGM2 and was named PGM2 i. Its corresponding control strain was Control i (Table 11).

The effect of PGM2 copy number on PGM specific activity was assessed in crude extracts of cells grown on galactose or glucose. On galactose grown cells, strains Control m and Control i displayed similar specific PGM activity, 0.33 and 0.34 U/mg protein, respectively, whereas the specific activity in PGM2 m and PGM2 i strains increased to 10.40 and 1.81 U/mg protein, respectively. In glucose grown cells specific PGM activity had lower values than in galactose grown cells. In glucose grown cells strains Control m and Control i displayed specific PGM activity of 0.23 and 0.10 U/mg protein, respectively, whereas the specific activity in PGM2 m and PGM2 i strains increased to 4.29 and 1.47 U/mg protein, respectively.

This is an example of a study of gene dosage under the control of HXT7 truncated promoter (Hauf, Zimmermann et al. 2000) and the effect shown was an increase of the PGM activity produced by additional copies of the PGM2 gene. Specific PGM activity was also assessed on glucose grown cells, which is a commonly found sugar in lignocellulosic hydrolysate.

References

Bro, C., S. Knudsen, et al. (2005). "Improvement of galactose uptake in *Saccharomyces cerevisiae* through overexpression of phosphoglucomutase: example of transcript analysis as a tool in inverse metabolic engineering." *Appl Environ Microbiol* 71(11): 6465-72.

Hauf, J., F. K. Zimmermann, et al. (2000). "Simultaneous genomic overexpression of seven glycolytic enzymes in the yeast *Saccharomyces cerevisiae*." *Enzyme Microb Technol* 26(9-10): 688-698.

Example 11

Construction of Strains with Genomic Integration of PGM2 and XYL1(K270R) Under the Control of Constitutive Promoters Strains and Medium Yeast strains and plasmids used in this study are summarized in Table 13. *Escherichia coli* DH5α (Life Technologies, Rockville, Md., USA) was used for sub-cloning. All strains were stored at −80° C. in 15% glycerol. *E. coli* was grown in LB medium (Sambrook J, Fritch E et al. 1989) with 100 mg·l$^{-1}$ ampicillin. Yeast strains from frozen stocks were streaked on YNB medium (6.7 g·l$^{-1}$ Difco Yeast Nitrogen Base without amino acids; Becton, Dickinson and Company, Sparks, Md., USA) supplemented with 20 g·l$^{-1}$ glucose, 20 g·l$^{-1}$ agar (Merck, Darmstadt, Germany) and a supplement of aminoacid/s was added when needed for auxotrophic strains (Hahn-Hägerdal, Karhumaa et al. 2005). Liquid medium was buffered at pH 5.5 for aerobic cultivations with 50 mM potassium hydrogen phthalate (Merck, Darmstadt, Germany) (Hahn-Hägerdal, Karhumaa et al. 2005) with 20 g·l$^{-1}$ glucose.

Molecular Biology Techniques

All enzymes used for cloning and restriction cleavage were obtained from Fermentas (Vilnius, Lithuania) otherwise stated. Analytical PCR was performed with Dream Taq™ Polymerase while preparative PCR before ligation or sequencing was performed with High Fidelity PCR Enzyme mix or Pwo Polymerase (Roche Diagnostics GmbH, Mannheim, Germany).

Plasmid DNA was isolated from bacteria with the GeneJET™ Plasmid Miniprep Kit from Fermentas (Vilnius, Lithuania). Purification of DNA products after restriction cleavage or PCR amplification was performed with the E.Z.N.A.® Cycle-Pure Kit (Omega Bio-tek Inc, Doraville, Ga., USA). The method used for bacterial transformation was the calcium chloride method (Dagert and Ehrlich 1979) and yeast transformation was carried out by the lithium acetate method (Gietz, Schiestl et al. 1995). Primer synthesis and sequencing was performed by Eurofins MWG Operon (Ebersberg, Germany). Yeast chromosomal DNA extraction was carried out by phenol/chloroform method.

Construction of Strains TMB 3143 and TMB 3144

Figure 7:
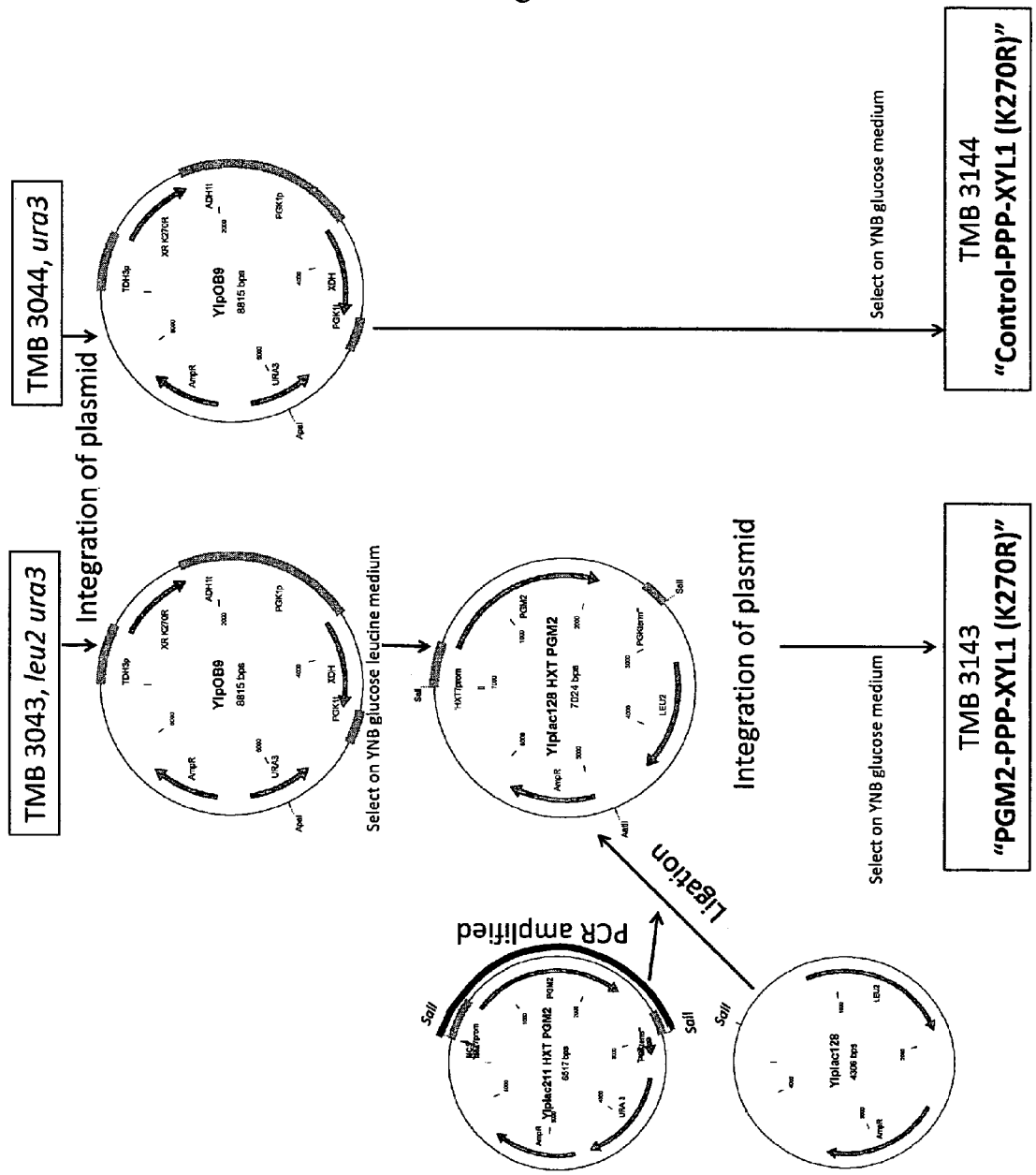
FIG. 7. Construction of strains with overexpressed PGM2 and XYL1(K270R)

*S. cerevisiae* strains TMB 3043 and TMB 3044 that have upregulated non-oxidative pentose phosphate pathway and deleted GRE3 gene (Karhumaa, Hahn-Hägerdal et al. 2005) were used as background strains to construct strains TMB 3143 ("PGM2-PPP-XYL1(K270R)") and TMB 3144 ("Control-PPP-XYL1(K270R)") respectively (Table 13) (FIG. 7). In practice, plasmid YlpOB9 (Table 13) was cleaved with ApaI within URA3 gene and used to transform yeast strains TMB 3043 and TMB 3044. Transformants were selected on YNB glucose medium supplemented with 60 mg·l$^{-1}$ leucine (Hahn-Hägerdal, Karhumaa et al. 2005) and on YNB glucose medium respectively (FIG. 7).

A positive clone of TMB 3043 with integrated YlpOB9 was further transformed with the linearized plasmid YIplac128 HXT-PGM2 and selection of transformants was carried out on YNB glucose plates.

The construction of YIplac128 HXT-PGM2 was made from plasmid YIplac128 and part of plasmid YIplac211 HXT-PGM2 (Table 13)(FIG. 7). YIplac128 plasmid was digested with SalI. The DNA cassette HXT7p PGM2 PGK1 t was PCR amplified having as template plasmid YIplac 211 HXT PGM2 (Table 13) and using primers PGK SalI and HXT SalI (Table 14) which were including the restriction site SalI at the ends of the amplified DNA cassette. The PCR product of HXT7p PGM2 PGK1 t was then digested with SalI restriction enzyme. Ligation of the SalI digested YIplac128 plasmid and the DNA cassette HXT7p PGM2 PGK1 t that included SalI sites resulted in plasmid YIplac 128 HXT-PGM2 (Table 13) (FIG. 7).

YIplac128 HXT-PGM2 (Table 13) was linearized by restriction cleavage with AatII enzyme and used to transform strain TMB 3043 with an already integrated copy of YIpOB9.

Transformants were confirmed first by PCR amplification and then by sequencing of the chromosomally integrated genes which were PCR amplified with a proofreading DNA polymerase from extracted genomic DNA.

TABLE 13

Strains and plasmids used in EXAMPLE 11

| *S. cerevisiae* strains | Strain background | Relevant genotype | Reference |
| --- | --- | --- | --- |
| TMB 3043 | TMB 3042 | CEN.PK2-1C, Δgre3 his3::HIS3 PGK1p-XK1-PGK1t, PGK1p-TAL1-PGK1t, PGK1p-RKI1-PGK1t, PGK1p-TKL1-PGK1t, PGK1p-RPE1-PGK1t, TRP1, leu2 ura3 | (Karhumaa, Hahn-Hägerdal et al. 2005) |
| TMB 3044 | TMB 3043 | CEN.PK2-1C, Δgre3 his3::HIS3 PGK1p-XK1-PGK1t, PGK1p-TAL1-PGK1t, PGK1p-RKI1-PGK1t, PGK1p-TKL1-PGK1t, PGK1p-RPE1-PGK1t, TRP1, ura3 | (Karhumaa, Hahn-Hägerdal et al. 2005) |

TABLE 13-continued

Strains and plasmids used in EXAMPLE 11

| TMB 3143 "PGM2-PPP-XYL1 (K270R)" | TMB 3043, TRP1 leu2 ura3 | YlpOB9, Ylplac128 HXT-PGM2 |
|---|---|---|
| TMB 3144 "Control-PPP-XYL1 (K270R)" | TMB 3044, TRP1 LEU2 ura3 | YlpOB9 |

| Plasmids | Relevant genotype | Reference |
|---|---|---|
| YlpOB9 | TDH3p-XYL1 (K270R)-ADH1t, PGK1p-XYL2-PGK1t, URA3 | (Bettiga, Bengtsson et al. 2009) |
| Ylplac128 | LEU2 | (Gietz and Sugino 1988) |
| Ylplac211 HXT-PGM2 | Ylplac211, HXT7p-PGM2-PGKt URA3 | |
| Ylplac128 HXT-PGM2 | Ylplac128, HXT7p-PGM2-PGKt LEU2 | |

TABLE 14

Primer list

| Primer | Sequence (5' to 3') | Characteristics of the sequence |
|---|---|---|
| PGK SalI | ATCTGTCGACGAACATAGAA ATATCGAATGG (SEQ. ID. NO. 24) | Underlined sequence homologous to PGKt. Restriction enzyme site in bold. |
| HXT SalI | ATCTGTCGACAGGAACAATT TCGGGCC (SEQ. ID. NO. 25) | Underlined sequence homologous to HXT7′ p. Restriction enzyme site in bold. |
| XR RV | TAGACGAAGATAGGAATC (SEQ. ID. NO. 26) | For analytical PCR or preparative PCR for sequencing |
| TDH3p FW | GTTTATCATTATCAATACTC (SEQ. ID. NO. 27) | For analytical PCR or preparative PCR for sequencing |
| HXT | CATCAAGAACAAACAAGCTC (SEQ. ID. NO. 28) | For analytical PCR or preparative PCR for sequencing |
| PGM2 RV3 | CGTTGGTTCTTCAGTTCC (SEQ. ID. NO. 29) | For analytical PCR or preparative PCR for sequencing |
| XR FW | GCCTTCTATTAAGTTGAAC (SEQ. ID. NO. 30) | For analytical PCR |

References

Bettiga, M., O. Bengtsson, et al. (2009). "Arabinose and xylose fermentation by recombinant *Saccharomyces cerevisiae* expressing a fungal pentose utilization pathway." Microbial Cell Factories 8: -.

Dagert, M. and S. D. Ehrlich (1979). "Prolonged incubation in calcium chloride improves the competence of *Escherichia coli* cells." Gene 6(1): 23-28.

Garcia Sanchez R., Hahn-Hägerdal B., et al. (Manuscript in preparation 2008). "PGM2 overexpression improves fermentation of galactose and/or xylose."

Garcia Sanchez R., Hahn-Hägerdal B., et al. (Manuscript in preparation 2009). "Improvement of xylose utilization in *Saccharomyces cerevisiae* strains overexpressing PGM2."

Gietz, R. D., R. H. Schiestl, et al. (1995). "Studies on the transformation of intact yeast cells by the LiAc/SS-DNA/PEG procedure." Yeast 11(4): 355-60.

Gietz, R. D. and A. Sugino (1988). "New yeast-*Escherichia coli* shuttle vectors constructed with in vitro mutagenized yeast genes lacking six-base pair restriction sites." Gene 74(2): 527-34.

Hahn-Hägerdal, B., K. Karhumaa, et al. (2005). "Role of cultivation media in the development of yeast strains for large scale industrial use." Microb Cell Fact 4: 31.

Karhumaa, K., B. Hahn-Hägerdal, et al. (2005). "Investigation of limiting metabolic steps in the utilization of xylose by recombinant *Saccharomyces cerevisiae* using metabolic engineering." Yeast 22(5): 359-68.

Sambrook J, Fritch E, et al. (1989). "Molecular Cloning: A Laboratory Manual." Cold Spring Harbor Laboratory Press: Cold Spring Harbor, N.Y.

Example 12

Characterization of Strains Overexpressing PGM2 and XYL1 (K270R)

Aerobic Cultivations

Yeast Nitrogen Base medium (YNB) (6.7 g·l$^{-1}$ Difco Yeast Nitrogen Base without aminoacids; Becton, Dickinson and Company, Sparks, Md., USA) was used for aerobic cultivations. It was supplemented either with 50 g·l$^{-1}$ xylose or 20 g·l$^{-1}$ glucose. YNB medium was buffered with potassium hydrogen phthalate (10.21 g·l$^{-1}$ phthalate, 2.1 g·l$^{-1}$ KOH, pH 5.5)(Hahn-Hägerdal, Karhumaa et al. 2005) for liquid medium and for plates 20 g l$^{-1}$ agar was added. The concentration of YNB was doubled when the sugar concentration exceeded 20 g l$^{-1}$. Pre-cultures grown in YNB with 20 g·l$^{-1}$ glucose until mid-late exponential phase on 50 ml tubes with 5 ml growth medium were used to inoculate aerobic batch cultures with 50 g l$^{-1}$ xylose at OD$_{620\,nm}$0.1-0.2 in cotton-stoppered baffled 500 ml flasks with 50 ml growth medium. Aerobic growth cultures were performed at least in biological duplicates and with a starting medium that was 10% of the volume of the flask.

Anaerobic Fermentation

Cells were pre-cultivated aerobically on defined mineral medium (Jeppsson, Bengtsson et al. 2006) with 20 g·l$^{-1}$ glucose and also buffered at pH 5.5 with 50 mM potassium hydrogen phthalate (Hahn-Hägerdal, Karhumaa et al. 2005). Anaerobic fermentation was carried out on the same defined mineral medium but supplemented with 50 g·l$^{-1}$ xylose, 0.4 g·l$^{-1}$ Tween 80 and 0.01 g·l$^{-1}$ ergosterol, and the pH was controlled by automatic addition of 3M KOH. The concentration of medium components was doubled because the sugar concentration exceeded 20 g·l$^{-1}$ sugar.

Pre-cultures were grown at 30° C. on an incubator (INR-200, Gallenkamp, Leicester, United Kingdom) at 180 rpm. A freshly streaked plate with yeast was used to inoculate a first 5 ml pre-culture into a test tube. Exponentially growing cells from the first pre-culture were used to inoculate a second pre-culture in a 1000 ml shake flask. Late exponentially growing cells were harvested by centrifuging 5 min at 4000 rpm, and washed with water before being used as inoculum for anaerobic batch in 2-1 Biostat®A bioreactors (B. Braun Biotech International, Melsungen, Germany) with a working volume of 1.5 l. Anaerobic conditions were attained by sparging nitrogen gas containing less than 5 ppm of O$_2$ (AGA Gas, Sundbyberg, Sweden) from the botton of the bioreactor at a flow rate of 0.2 l min$^{-1}$ controlled by a gas mass flow-meter (Bronkhorst, HI-TECH, Ruurlo, The Netherlands). Dissolved oxygen was monitored by a probe. Outlet carbon dioxide and oxygen was monitored by an INNOVA 1313 fermentation monitor (LumaSense Technologies, Ballerup, Denmark). Anaerobic fermentation experiments were performed at least in biological duplicates. All physiological characterization of strains was performed with prototrophic strains for proper comparison of all the parameters.

Results

Strains TMB 3143 ("PGM2-PPP-XYL1(K270R)") and TMB 3144 ("Control-PPP-XYL1(K270R)") were constructed to assess the influence of PGM2 overexpression on xylose utilization by recombinant S. cerevisiae strains. Heterologous expression of integrated copies of PGM2 and XYL1 (K270R) were under the control of constitutive promoters, the truncated HXT7 (Hauf, Zimmermann et al. 2000) and TDH3p respectively. Strain PGM2-PPP-XYL1(K270R), increased the flux through the xylose utilization pathway under both aerobic and anaerobic conditions.

Figure 8:
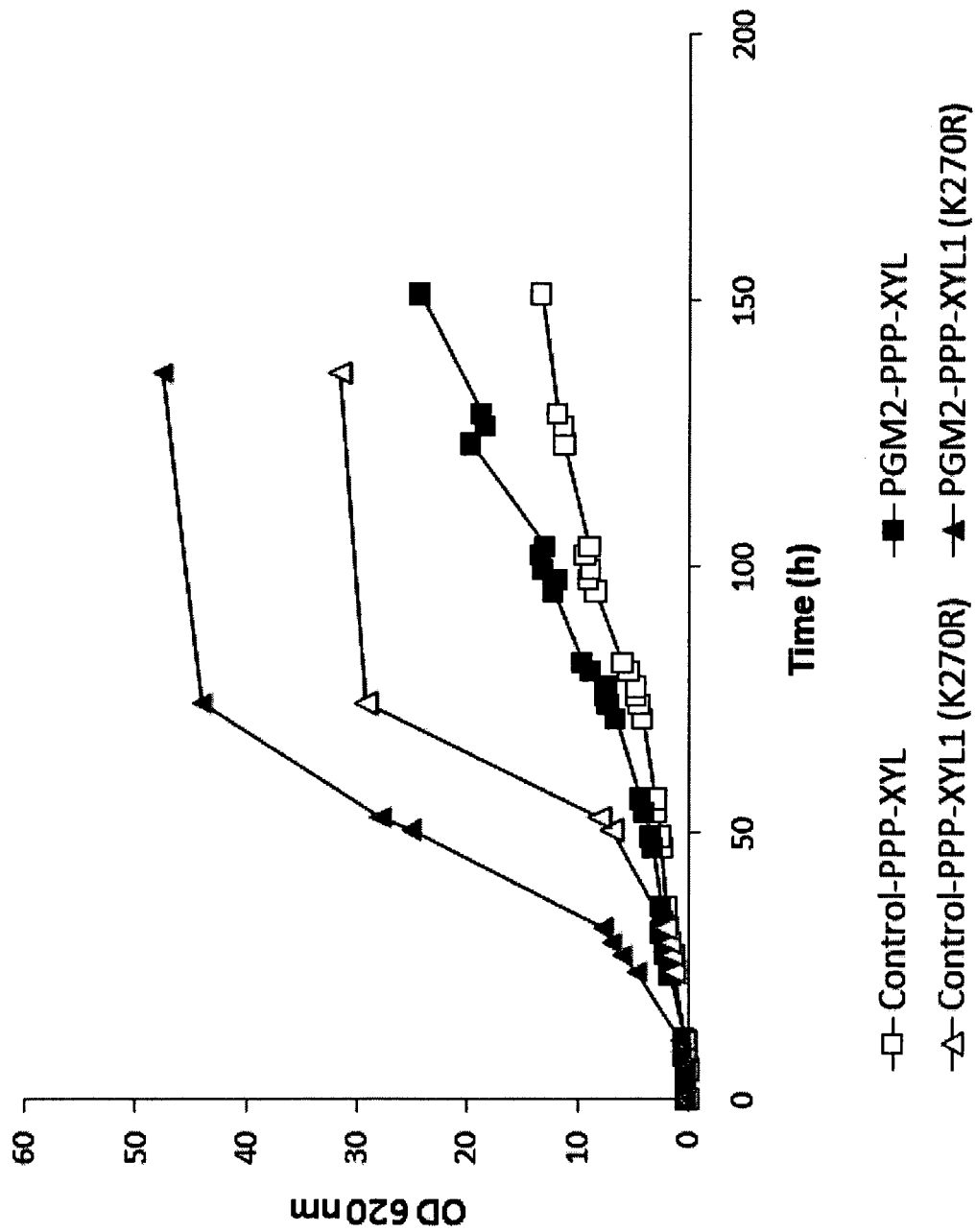
FIG. 8. Aerobic growth on YNB medium supplemented with 50 g $l^{-1}$ xylose and with cells pre-grown on YNB medium supplemented with 20 g $l^{-1}$ glucose. Strains used: Control-PPP-XYL (TMB 3137) (□), PGM2-PPP-XYL (TMB 3138) (■), Control-PPP-XYL1(K270R) (TMB 3144) (△) and PGM2-PPP-XYL1(K270R) (TMB 3143) (▲)

Strain PGM2-PPP-XYL1(K270R) grew in aerobic batch in medium with xylose (50 g·l$^{-1}$) as the sole carbon source at a maximum exponential growth rate ($\mu^{max}$) of 0.180±0.027 h$^{-1}$ while strain Control-PPP-XYL1(K270R) had $\mu^{max}$ of 0.123±0.029 h$^{-1}$ (FIG. 8) (Table 15). The final OD$_{620\,nm}$ was 48.0±0.5 for strain PGM2-PPP-XYL1(K270R) and 34.9±1.8 for strain Control-PPP-XYL1(K270R). The final biomass was then 27% higher for strain PGM2-PPP-XYL1(K270R) (FIG. 8).

Strains Control-PPP-XYL (TMB 3137) and PGM2-PPP-XYL (TMB 3138) were also included in the comparison experiment of aerobic growth on medium with xylose (50 g l$^{-1}$) (FIG. 8) (Table 15). Wild type XR showed a lower growth capacity on xylose. $\mu^{max}$ was of 0.038±0.014 h$^{-1}$ for strain Control-PPP-XYL1 and strain PGM2-PPP-XYL had $\mu^{max}$ of 0.041±0.008 h$^{-1}$ (FIG. 8)(Table 15).

The results show that integration of either PGM2 and/or XYL1(K270R) under the control of constitutive promoters improved growth on xylose medium (FIG. 8)(Table 15). This effect was additive when both genes were integrated in the genome of the same strain, in our case shown in strain PGM2-PPP-XYL (K270R) (FIG. 8).

Figure 9:
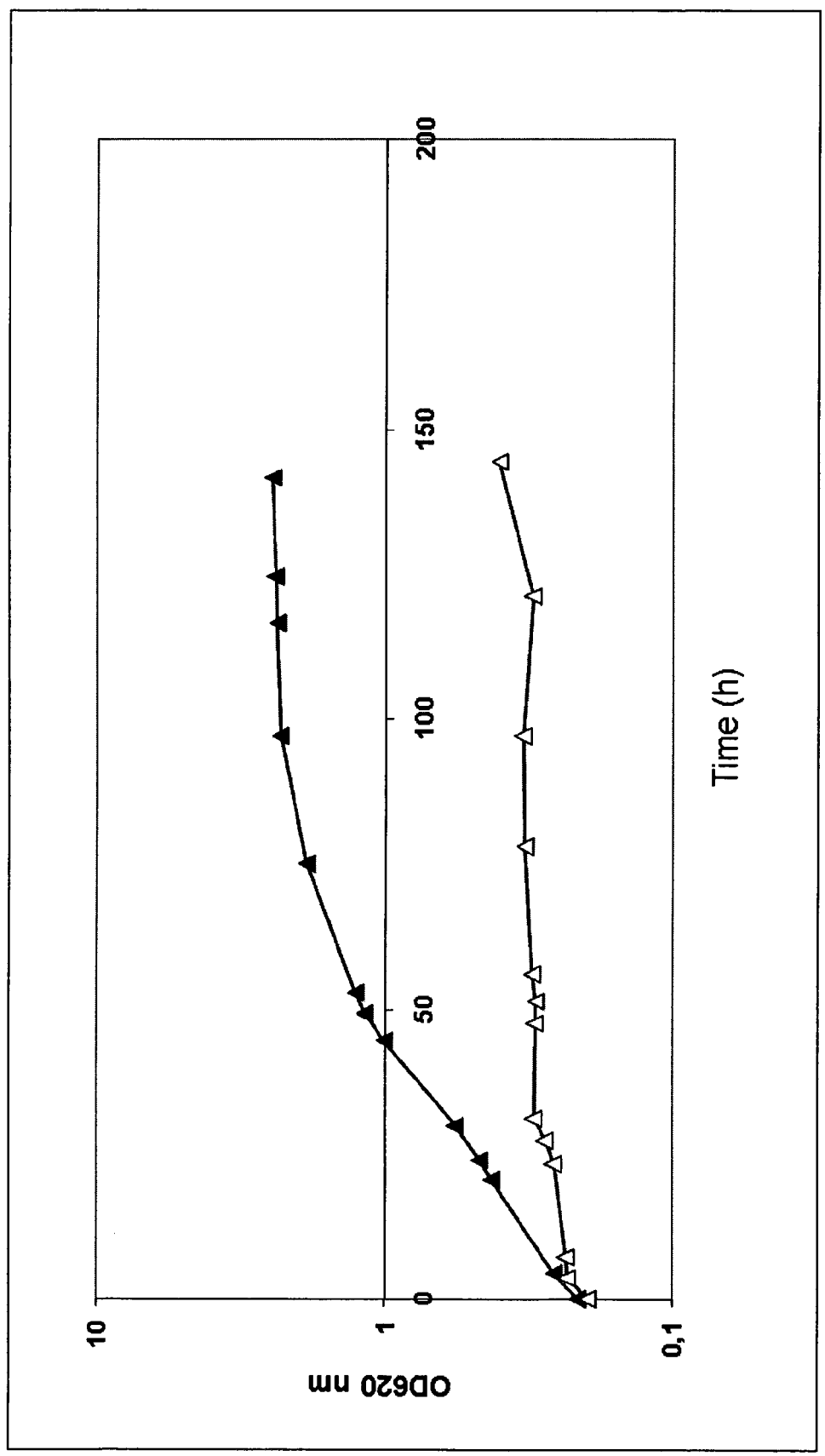
FIG. 9. Anaerobic fermentation on 50 g $l^{-1}$ xylose with pre-culture on medium supplemented with 20 g $l^{-1}$ glucose. Strains used: Control-PPP-XYL1(K270R) (TMB 3144) (△) and PGM2-PPP-XYL1(K270R) (TMB 3143) (▲)

Anaerobic fermentation on 50 g·l$^{-1}$ xylose as the sole carbon source showed that strain PGM2-PPP-XYL1(K270R) has an improved growth rate (0.060±0.025 h$^{-1}$) by a factor of four comparing to that of strain Control-PPP-XYL1(K270R) (0.015±0.008 h$^{-1}$) (FIG. 9). Strain PGM2-PPP-XYL1(K270R) that additionally had an extra copy of constitutively expressed PGM2 gene, showed an additional improvement of anaerobic growth on xylose.

Ethanol production from xylose was improved for strain PGM2-PPP-XYL1(K270R) (Table 16). Ethanol yields/concentrations are calculated from the raw data of detected ethanol. The ethanol yield (g of ethanol g of xylose consumed$^{-1}$) was 0.33±0.03 for strain Control-PPP-XYL1(K270R) and 0.37±0.01 for strain PGM2-PPP-XYL1(K270R). The ethanol yield (g of ethanol g of produced biomass$^{-1}$) was 4.31±0.26 for strain Control-PPP-XYL1(K270R) and 9.38±1.88 for strain PGM2-PPP-XYL1(K270R). The final ethanol titer was 0.90±0.52 for strain Control-PPP-XYL1(K270R) and 3.17±0.57 for strain PGM2-PPP-XYL1(K270R).

Strain PGM2-PPP-XYL1(K270R) had higher xylitol yield (0.22±0.01) than that of strain Control-PPP-XYL1(K270R) (0.08±0.07) (Table 2) due to a higher amount of total xylose consumed (data not shown).

Biomass yield (g biomass g consumed xylose$^{-1}$) was double for strain Control-PPP-XYL1(K270R) (0.08±0.00) in comparison to that of strain PGM2-PPP-XYL1(K270R) (0.04±0.01).

The acetate and glycerol yield from xylose was very similar for strains Control-PPP-XYL1(K270R) and PGM2-PPP-XYL1(K270R). The acetate yield was of the order of 0.01 g acetate g consumed xylose$^{-1}$ and the glycerol yield was between 0.03 and 0.04 g glycerol g consumed xylose$^{-1}$.

TABLE 15

Maximum specific growth rate $\mu^{max}$ (h$^{-1}$) on aerobic batch culture on YNB medium with xylose (50 g l$^{-1}$) with cells pre-grown on YNB medium with glucose (20 g l$^{-1}$).

| Strain | $\mu^{max}$ (h$^{-1}$) |
| --- | --- |
| Control-PPP-XYL | 0.038 ± 0.014 |
| PGM2-PPP-XYL | 0.041 ± 0.008 |
| Control-PPP-XYL1(K270R) | 0.123 ± 0.029 |
| PGM2-PPP-XYL1(K270R) | 0.180 ± 0.027 |

TABLE 16

Metabolite production during anaerobic growth on xylose

| Strain | Ethanol yield (g ethanol g consumed xylose$^{-1}$) | Ethanol yield (g ethanol g produced biomass$^{-1}$) | Ethanol titer (g produced ethanol l$^{-1}$) | Xylitol yield (g xylitol g consumed xylose$^{-1}$) | Biomass yield (g biomass g consumed xylose$^{-1}$) |
|---|---|---|---|---|---|
| Control-PPP-XYL1(K270R) | 0.33 ± 0.03 | 4.31 ± 0.26 | 0.90 ± 0.52 | 0.08 ± 0.07 | 0.08 ± 0.00 |
| PGM2-PPP-XYL1(K270R) | 0.37 ± 0.01 | 9.38 ± 1.88 | 3.17 ± 0.57 | 0.22 ± 0.01 | 0.04 ± 0.01 |

References

Hahn-Hägerdal, B., K. Karhumaa, et al. (2005). "Role of cultivation media in the development of yeast strains for large scale industrial use." Microb Cell Fact 4: 31.

Hauf, J., F. K. Zimmermann, et al. (2000). "Simultaneous genomic overexpression of seven glycolytic enzymes in the yeast *Saccharomyces cerevisiae*." Enzyme Microb Technol 26(9-10): 688-698.

Jeppsson, M., O. Bengtsson, et al. (2006). "The expression of a *Pichia stipitis* xylose reductase mutant with higher K(M) for NADPH increases ethanol production from xylose in recombinant *Saccharomyces cerevisiae*." Biotechnol Bioeng 93(4): 665-73.

Runquist, D., B. Hahn-Hagerdal, et al. (2009). "Increased expression of the oxidative pentose phosphate pathway and gluconeogenesis in anaerobically growing xylose-utilizing *Saccharomyces cerevisiae*." Microbial Cell Factories 8(1): 49.

Example 13

Construction of Industrial Xylose Consuming Strains with Genomic Integration of PGM2 Gene Under the Control of a Constitutive Promoter Strains and Medium Yeast strains and plasmids used in this study are summarized in Table 17. *Escherichia coli* DH5α (Life Technologies, Rockville, Md., USA) was used for sub-cloning. All strains were stored at −80° C. in 15% glycerol. *E. coli* was grown in LB medium (Sambrook J, Fritch E et al. 1989) with 100 mg·l$^{-1}$ ampicillin. Yeast strains from frozen stocks were streaked on YNB medium (6.7 g·l$^{-1}$ Difco Yeast Nitrogen Base without amino acids; Becton, Dickinson and Company, Sparks, Md., USA) or YPD (10 g l$^{-1}$ yeast extract, 20 g l$^{-1}$ peptone) supplemented with 20 g l$^{-1}$ glucose, 20 g l$^{-1}$ agar (Merck, Darmstadt, Germany). YPD plates were supplemented with geneticin (Gibco Invitrogen, Paisley, UK) when needed at concentrations of 150 or 200 mg l$^{-1}$. Liquid medium was buffered at pH 5.5 for aerobic cultivations with 50 mM potassium hydrogen phthalate (Merck, Darmstadt, Germany) (Hahn-Hägerdal, Karhumaa et al. 2005) with 20 g l$^{-1}$ glucose.

Molecular Biology Techniques

All enzymes used for cloning and restriction cleavage were obtained from Fermentas (Vilnius, Lithuania). Analytical PCR was performed with Dream Taq™ Polymerase while preparative PCR before ligation, integration or sequencing was performed with High Fidelity PCR Enzyme.

Plasmid DNA was isolated from bacteria with the GeneJET™ Plasmid Miniprep Kit from Fermentas (Vilnius, Lithuania). Purification of DNA products after restriction cleavage or PCR amplification was performed with the E.Z.N.A.® Cycle-Pure Kit (Omega Bio-tek Inc, Doraville, Ga., USA). QIAquick® Gel Extraction Kit (Qiagen GmbH, Hilden, Germany) was used for DNA extraction from agarose gel. The method used for bacterial transformation was the calcium chloride method (Dagert and Ehrlich 1979) and yeast transformation was carried out by the lithium acetate method (Gietz, Schiestl et al. 1995). Primer synthesis and sequencing was performed by Eurofins MWG Operon (Ebersberg, Germany).

Results

Plasmid Construction

Figure 10:
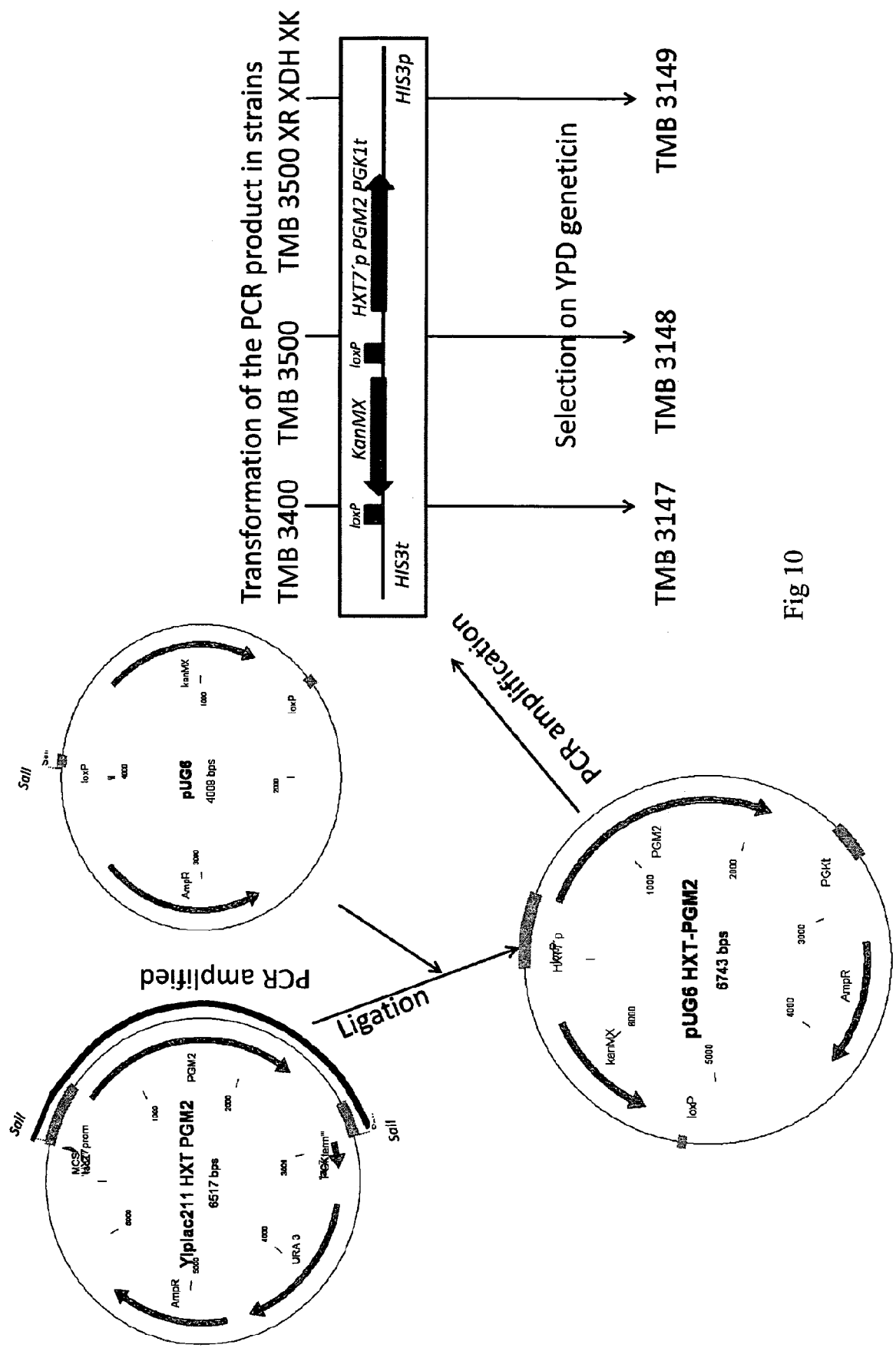
FIG. 10. Construction of xylose industrial strains with PGM2 overexpression

The DNA cassette HXT7p PGM2 PGK1 t was PCR amplified having as template plasmid YIplac 211 HXT PGM2 (Table 17) and using primers PGK SalI and HXT SalI (Table 18) which were including the restriction site SalI at the ends of the amplified DNA cassette (FIG. 10). The PCR product of HXT7p PGM2 PGK1 t was then digested with SalI restriction enzyme. The resulting purified DNA fragment was inserted into the plasmid pUG6 which has been also cleaved with the restriction enzyme SalI, creating pUG6 HXT-PGM2 (Table 17) (FIG. 10).

Construction of Strains TMB 3147, TMB 3148 and TMB 3149

The DNA cassette HXT7p PGM2 PGK1 t KanMX was PCR amplified having as template plasmid pUG6 HXT-PGM2 (Table 17) and using primers HIS3p-HXT7p FW and HIS3t-loxP RV (Table 18) which were including overhangs homologous to the HIS3 promoter and terminator of the yeast HIS3 gene to facilitate integration of the DNA cassette in the HIS3 locus of *S. cerevisiae* genome (FIG. 10).

The purified DNA cassette HXT7p PGM2 PGK1 t KanMX with HIS3 overhangs was used to transform *S. cerevisiae* strains TMB 3400, TMB 3500 and TMB 3500 XR/XDH/XK, resulting in strains TMB 3147, TMB 3148 and TMB 3149 respectively (FIG. 10).

Transformants were selected on YPD plates supplemented with geneticin. Positive tranformants were confirmed first by PCR amplification and then by sequencing of the chromosomally integrated genes which were PCR amplified with a proofreading DNA polymerase from extracted genomic DNA.

TABLE 17

Strains and plasmids used in EXAMPLE 13

| | Relevant genotype | Reference |
|---|---|---|
| *S. cerevisiae* strains | | |
| TMB 3400 | HIS3:: ADH1p XYL1 ADH1t, PGK1p XYL2 PGK1t, PGK1p XKS1 PGK1t | (Wahlbom, van Zyl et al. 2003) |
| TMB 3500 | | (Almeida; unpublished) |
| TMB 3500 XR/XDH/XK | TMB 3500, HIS3:: YIpXR/XDH/XK | (Almeida; unpublished) |
| TMB 3147 | TMB 3400 HIS3:: HXT7'p PGM2 PGK1t KanMX | (Garcia Sanchez R., Hahn-Hägerdal B. et al. Unpublished work) |
| TMB 3148 | TMB 3500 HIS3:: HXT7'p PGM2 PGK1t KanMX | (Garcia Sanchez R., Hahn-Hägerdal B. et al. Unpublished work) |
| TMB 3149 | TMB 3500, HIS3:: YIpXR/XDH/XK, HXT7'p PGM2 PGK1t KanMX | (Garcia Sanchez R., Hahn-Hägerdal B. et al. Unpublished work) |
| Plasmids | | |
| YIpXR/XDH/XK | ADH1p XYL1 ADH1t, PGK1p XYL2 PGK1t, PGK1p XKS1 PGK1t, HIS3 | (Eliasson, Christensson et al. 2000) |
| YIplac 211 HXT-PGM2 | YIplac211, HXT7p-PGM2-PGKt URA3 | (Garcia Sanchez R., Hahn-Hägerdal B. et al. Manuscript in preparation 2009) |
| pUG6 | KanMX | (Güldener, Heck et al. 1996) |
| pUG6 HXT-PGM2 | HXT7'p PGM2 PGK1t KanMX | (Garcia Sanchez R., Hahn-Hägerdal B. et al. Unpublished work) |

TABLE 18

Primer list

| Primer | Sequence (5' to 3') | Characteristics of the sequence |
|---|---|---|
| PGK SalI | ATCTGTCGACGAACATAGAAATATCGAATGG (SEQ. ID. NO. 31) | Underlined sequence homologous to PGKt. Restriction enzyme site in bold. |
| HXT SalI | ATCTGTCGACAGGAACAATTTCGGGCC (SEQ. ID. NO. 32) | Underlined sequence homologous to HXT7' p. Restriction enzyme site in bold. |
| HIS3p-HXT7p FW | CTTAGCGATTGGCATTATCACATAATGATTGCTGAAGCTTCGTACGC (SEQ. ID. NO. 33) | Underlined part is homologous to the promoter of HIS3 gene and not underlined part is homologous to the sequence in pUG6 HXT-PGM2 at 3' end of the sequence HXT7' p PGM2 PGK1t |
| HIS3t-loxP RV | TGACACGTATAGAATGATGCATTACCTTGTCCGGCAGATCCGCGG (SEQ. ID. NO. 34) | Underlined sequence is homologous to the terminator of HIS3 gene and not underlined is homologous to the sequence of pUG6 HXT-PGM2 at loxP site position at 3' of KanMX. |

References

Almeida, J. R. M. "Unpublished work."

Dagert, M. and S. D. Ehrlich (1979). "Prolonged incubation in calcium chloride improves the competence of *Escherichia coli* cells." Gene 6(1): 23-28.

Eliasson, A., C. Christensson, et al. (2000). "Anaerobic xylose fermentation by recombinant *Saccharomyces cerevisiae* carrying XYL1, XYL2, and XKS1 in mineral medium chemostat cultures." Appl Environ Microbiol 66(8): 3381-6.

Garcia Sanchez R., Hahn-Hägerdal B., et al. (Unpublished work). "Construction of an industrial xylose consuming strain with PGM2 overexpression".

Garcia Sanchez R., Hahn-Hägerdal B., et al. (Manuscript in preparation 2008). "PGM2 overexpression improves fermentation of galactose and/or xylose."

Gietz, R. D., R. H. Schiestl, et al. (1995). "Studies on the transformation of intact yeast cells by the LiAc/SS-DNA/PEG procedure." Yeast 11(4): 355-60.

Güldener, U., S. Heck, et al. (1996). "A new efficient gene disruption cassette for repeated use in budding yeast." Nucleic Acids Research 24(13): 2519-2524.

Hahn-Hägerdal, B., K. Karhumaa, et al. (2005). "Role of cultivation media in the development of yeast strains for large scale industrial use." Microb Cell Fact 4: 31

Sambrook J, Fritch E, et al. (1989). "Molecular Cloning: A Laboratory Manual." Cold Spring Harbor Laboratory Press: Cold Spring Harbor, N.Y.

Wahlbom, C. F., W. H. van Zyl, et al. (2003). "Generation of the improved recombinant xylose-utilizing *Saccharomyces cerevisiae* TMB 3400 by random mutagenesis and

Example 14

Generation of a Mutant XR Through Random Mutagenesis and Selection for Anaerobic Growth Strains and Cultivation Conditions S. cerevisiae strains and plasmids used in this study are summarized in Table 19. Escherichia coli was grown on liquid or solid (15 g/L agar) LB medium supplemented with 100 mg/L ampicillin. On solid medium S. cerevisiae strains were grown on YNB plates (6.7 g/L Yeast Nitrogen Base wo amino acids) supplemented with either 20 g/L glucose or 60 g/L xylose. Defined mineral medium was used for liquid cultivation of S. cerevisiae and was composed of: xylose 60 g/L (unless otherwise noted); mineral salts (($NH_4)_2SO_4$, 5 g/L; $KH_2PO_4$, 3 g/L; $MgSO_4.7H_2O$, 0.5 g/L); Tween 80 0.4 g $l^{-1}$; ergosterol 0.01 g $l^{-1}$ (Andreasen and Stier 1953); vitamins and trace elements (Verduyn et al. 1992). Identical medium was used for pre-culture and batch fermentation in instrumented bioreactor with the exception that 50 mM Potassium Pthalate pH 5.5 (Hahn-Hägerdal et al. 2005) was added as buffering agent in the former case. Batch cultivation was performed in an instrumented bioreactor (Applikon Biotechnology, AC Schiedam, the Netherlands) with 2 L working volume. The medium was prepared as previously described with antifoam (Dow Corning, Midland, USA) added to the reactor at a final concentration of 0.25 mL/L. Temperature was maintained at 30° C. and the pH was controlled at 5.5 through addition of 3 M KOH. During aerobic growth, the agitation rate was set to 900 rpm and the culture was sparged with air at 1 L/min. During anaerobic cultivation the agitation rate was reduced to 200 rpm and oxygen free conditions were maintained by nitrogen sparging at 0.2 L/min. $CO_2$ production was detected online by an INNOVA 1313 fermentation monitor (LumaSense Technologies, Ballerup, Denmark). Cultures were sampled for HPLC (High Performance Liquid Chromatography), $OD_{620nm}$ and cell dry-weight measurements.

Library Construction

A random library of Pichia stipitis XYL1 were generated by error-prone PCR and the MEGAWHOP strategy for whole plasmid synthesis (Miyazaki and Takenouchi 2002). Primers were constructed to amplify a region between +631 bp-+870 bp centered on the active site of XYL1. Error-prone PCR was conducted using Mutazyme II polymerase (Stratagene, Cedar Creek, Tex., USA) according to the manufacturer's instructions. The mutation frequency of the PCR reaction was set to 1.5-2 nt/amplicon by optimizing the amount of template DNA and verifying the error distribution by sequencing 7-10 transformants. Following error-prone PCR, the amplified DNA was purified using the E.Z.N.A Cycle-Pure kit (Omega Bio-tek, Doraville, Ga., USA) and used as "megaprimer" for reconstruction of the template plasmid. Whole plasmid PCR was carried out as previously described (Miyazaki and Takenouchi 2002) using YIpOB8 as template (Table 19). The following concentration of reagents were used (in 50 µL): 5 µL 10× pfu buffer, 0.25 mM dNTPs, 300 ng template plasmid, 250 ng megaprimer and 2.5 U native Pfu DNA polymerase (Fermentas, Vilnius, Lithuania). The cycle parameters where: 95° C. 2 min; 15-17 cycles of 95° C. 30 s, 60° C. 30 s, 68° C. 2 min/kb; 68° C. 7 min. Following PCR, the template DNA was digested by adding 1 µL FastDigest DpnI (Fermentas, Vilnius, Lithuania) and incubating for 1 hr at 37° C. The reconstructed mutated plasmid was concentrated by isopropanol precipitation and used to transform Escherichia coli. Transformation was performed using 80 µL Electro-10Blue competent cells (Stratagene, Cedar Creek, Tex., USA) and electroporation (17 kV/cm, 200 Ω, 25 µF) in a 0.1 cm cuvette (Dower et al. 1988). The size of the library was determined by plating a small volume of appropriately diluted cells on LB ampicilin (100 mg/L) plates. The rest of the transformed cells were inoculated in 2×250 mL liquid LB ampcillin (100 mg/L) medium and grown over night at 37° C. The resulting E. coli library was stored in 15% glycerol stocks at −80° C. while plasmid DNA was harvested using the QIAfilter Plasmid Mega Kit (Qiagen, Hilden, Germany). The mutated plasmid library was used for large scale transformation (Gietz and Schiestl 2007) of Saccharomyces cerevisiae strain TMB 3044 (Table 19). The mutated plasmid library was linearized using EcoRV for integrative transformation.

Selection of the S. cerevisiae XYL1 Library

Following large-scale transformation of TMB 3044 (Table 19), cells were inoculated in an instrumented bioreactor for selection in liquid mineral medium (glucose 5 g/L and xylose 55 g/L) during aerobic conditions. After approximately 48 hrs, cell growth had reached $\sim OD_{620\ nm}=40$ and initial selection of the transformed S. cerevisiae library was completed. For selection of S. cerevisiae transformants carrying beneficial XYL1 mutations, conditions were changed to anaerobiosis and 95% of the culture medium was pumped out and exchanged for fresh medium (xylose 60 g/L). During anaerobic selection, cell growth was monitored through $CO_2$ production rate, optical density ($OD_{620\ nm}$) and aerobic and anaerobic growth on YNB-xylose plates. When the substrate in the reactor had been consumed, as monitored through the $CO_2$ production rate, 95% of the medium was pumped out and replaced with fresh medium.

Figure 11:
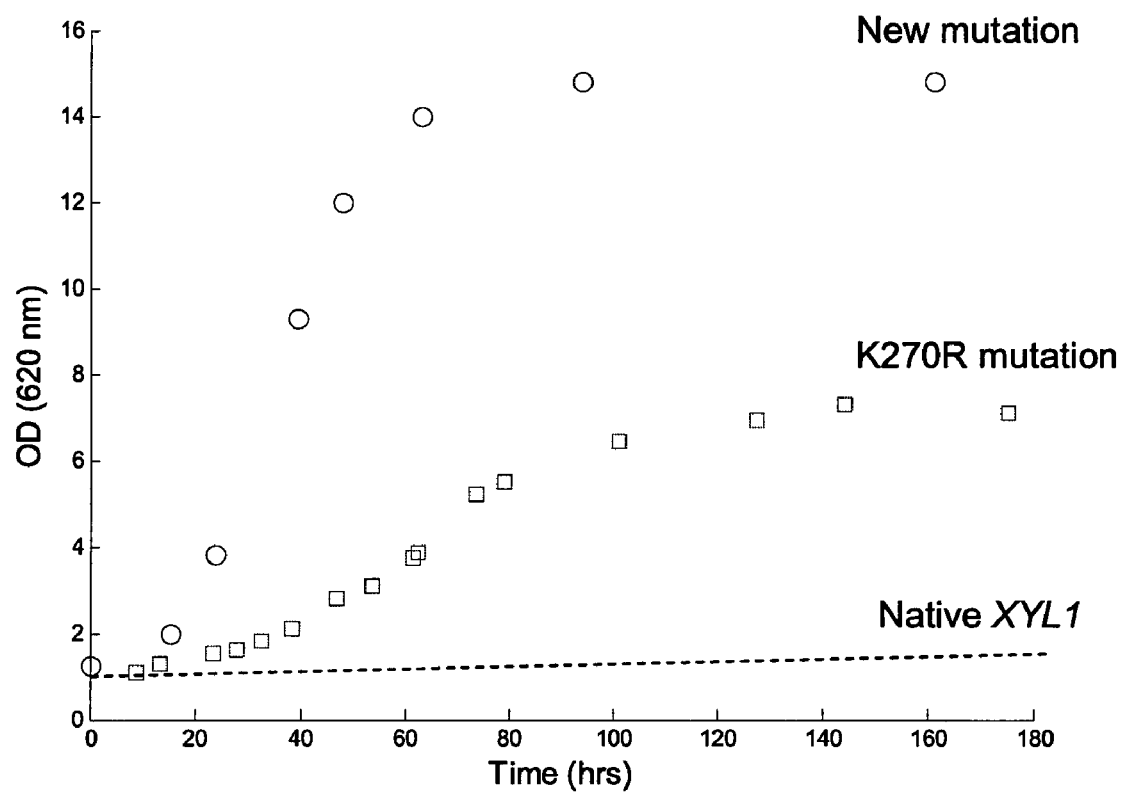
FIG. 11. Anaerobic growth on xylose as sole carbon source with the XYL1 gene isolated from the randomly generated sequence library.

Following 10 sequential batch cultivations under strictly anaerobic conditions, an isogenic population harbouring the same mutated XYL1 gene had been isolated. The mutated XYL1 sequence (Table 20) contained three nucleotide point mutations close to the previously characterized K270R mutation (cf example 4, 5, 6, 7) (Bengtsson et al. 2009). The mutated XYL1 gene substantially increased anaerobic growth and ethanol productivity during anaerobic batch cultivation on xylose as a sole carbon source (FIG. 11). Compared to the strain harbouring XR K270R with the previously highest ethanol productivity and growth rate (cf example 4, 5, 6, 7) (Runquist et al. 2009), the anaerobic growth rate was increased three times (FIG. 11). The current strain is thus the by far the best strain available for ethanol production from xylose.

References

Andreasen A A, Stier T J (1953) Anaerobic nutrition of Saccharomyces cerevisiae. I. Ergosterol requirement for growth in a defined medium. J Cell Physiol 41:23-36.

Bengtsson O, Hahn-Hägerdal B, Gorwa-Grauslund M F (2009) Xylose reductase from Pichia stipitis with altered coenzyme preference improves ethanolic xylose fermentation by recombinant Saccharomyces cerevisiae. Biotechnol Biofuels 2:9.

Dower W J, Miller J F, Ragsdale C W (1988) High efficiency transformation of E. coli by high voltage electroporation. Nucleic Acids Res 16:6127-45.

Gietz R D, Schiestl R H (2007) Large-scale high-efficiency yeast transformation using the LiAc/SS carrier DNA/PEG method. Nat Protoc 2:38-41.

Gietz R D, Sugino A (1988) New yeast-*Escherichia coli* shuttle vectors constructed with in vitro mutagenized yeast genes lacking 6-base pair restriction sites. Gene 74:527-534.

Hahn-Hägerdal B, Karhumaa K, Larsson C U, Gorwa-Grauslund M F, Gorgens J, van Zyl W H (2005) Role of cultivation media in the development of yeast strains for large scale industrial use. Microb Cell Fact 4:31.

Karhumaa K, Hahn-Hägerdal B, Gorwa-Grauslund M F (2005) Investigation of limiting metabolic steps in the utilization of xylose by recombinant *Saccharomyces cerevisiae* using metabolic engineering. Yeast 22:359-68.

Miyazaki K, Takenouchi M (2002) Creating random mutagenesis libraries using megaprimer PCR of whole plasmid. BioTechniques 33:1033-4, 1036-8.

Runquist D, Hahn-Hägerdal B, Bettiga M (2009) Increased expression of the oxidative pentose phosphate pathway and gluconeogenesis in anaerobically growing xylose-utilizing *Saccharomyces cerevisiae*. Microb Cell Fact 8:49.

Verduyn C, Postma E, Scheffers W A, van Dijken J P (1992) Effect of benzoic acid on metabolic fluxes in yeasts—a continuous culture study on the regulation of respiration and alcoholic fermentation. Yeast 8:501-517.

TABLE 19

*S. cerevisiae* strains and plasmids used in EXAMPLE 14.

| Plasmid and strains | Relevant features | Reference |
|---|---|---|
| Plasmids | | |
| YIplac128 | LEU2 | (Gietz and Sugino 1988) |
| YIpOB8 | URA3 TDH3p-XYL1-ADH1t, PGK1p-XYL2-PGK1t | |
| YIpDR6 | YIpOB8 XYL1 mutatated | This work |
| *S. cerevisiae* strains | | |
| TMB 3044 | CEN.PK 2-1C ΔGRE3, his3::PGK1p-XKS1-PGK1t, TAL1:PGK1p-TAL1-PGK1t, TKL1::PGK1p-TKL1-PGK1t, RKI1::PGK1p-RKI1-PGK1t, RPE1::PGK1p-RPE1-PGK1t, leu2::YIplac128, ura3 | (Karhumaa et al. 2005) |
| TMB 3422 | TMB 3044 YIpDR6 | This work |

The invention claimed is:

1. An isolated *Saccharomyces* sp. strain comprising a genome, the genome comprising:
   a) a xylose reductase gene having NADH-preference, wherein expression of said xylose reductase gene is controlled by a constitutive promoter,
   b) a xylitol dehydrogenase (XDH) gene, wherein said XDH gene is expressed, and
   c) a transaldolase gene, wherein expression of said transaldolase gene is increased as compared to the parental strain of the *Saccharomyces* sp. strain,
   wherein the *Saccharomyces* sp. strain grows on pentose sugars under anaerobic cultivation conditions.

2. The *Saccharomyces* sp. strain according to claim 1, wherein a gene encoding phosphoglucomutase activity is constitutively overexpressed in said strain.

3. The *Saccharomyces* sp. strain according to claim 1, wherein said constitutive promoter is selected from the group consisting of TDH3, HXT7, TEF1 and PGK1.

4. The *Saccharomyces* sp. strain according to claim 1, wherein said xylose reductase gene is derived from *Pichia stipitis* and the xylose reductase encoded by the gene comprises amino acid substitution K270R (XRK270R).

5. The *Saccharomyces* sp. strain according to claim 1, wherein said xylose reductase gene is derived from *Pichia stipitis* and the xylose reductase encoded by the gene comprises amino acid substitutions N272D and/or P275Q.

6. The *Saccharomyces* sp. strain according to claim 1, the genome further comprising a xylulokinase (XK) gene, wherein said XK gene is overexpressed.

7. The *Saccharomyces* sp. strain according to claim 1, having the nucleotide sequence as shown in SEQ ID NO: 1 and/or SEQ ID NO:2 and/or SEQ ID NO:3 integrated in the genome.

8. The *Saccharomyces* sp. strain according to claim 1, wherein said strain is selected from the group consisting of *Saccharomyces cerevisiae*, *Saccharomyces bayanus*, and *Saccharomyces carlsbergensis*.

9. The *Saccharomyces* sp. strain according to claim 1, wherein said strain is a polyploid or aneuploid industrial isolate.

10. The *Saccharomyces* sp. strain according to claim 8, wherein said strain is *Saccharomyces cerevisiae*.

* * * * *